United States Patent
Hammond et al.

(10) Patent No.: US 6,545,015 B2
(45) Date of Patent: Apr. 8, 2003

(54) CATECHOLS AS ANTIMICROBIAL AGENTS

(75) Inventors: Milton L. Hammond, Somerville, NJ (US); Aaron H. Leeman, Cranford, NJ (US); Milana Maletic, Hoboken, NJ (US); Gina M. Santorelli, Oceanport, NJ (US); Sherman T. Waddell, Westfield, NJ (US); John Finn, Stow, MA (US); Michael Morytko, Framingham, MA (US); Jason Hill, Auburndale, MA (US); Dennis Keith, Montclair, NJ (US)

(73) Assignee: Merck & Co., Inc., Rahway ( * ) Notice: Subject to any disclaimer, the term of this patent is extended or adjusted under 35 U.S.C. 154(b) by 0 days.

(21) Appl. No.: 09/934,743

(22) Filed: Aug. 22, 2001

(65) Prior Publication Data

US 2002/0040147 A1 Apr. 4, 2002

Related U.S. Application Data

(62) Division of application No. 09/566,275, filed on May 5, 2000.
(60) Provisional application No. 60/132,545, filed on May 5, 1999.

(51) Int. Cl.[7] ............................................. C07D 215/00
(52) U.S. Cl. ....................... 514/303; 546/118
(58) Field of Search ........................... 514/303; 546/118

(56) References Cited

U.S. PATENT DOCUMENTS

| | | |
|---|---|---|
| 3,854,480 A | 12/1974 | Zaffaroni |
| 4,452,775 A | 6/1984 | Kent |
| 5,041,567 A | 8/1991 | Rogers et al. |
| 5,239,660 A | 8/1993 | Ooi |
| 5,726,195 A | 3/1998 | Hill et al. |

FOREIGN PATENT DOCUMENTS

| | | |
|---|---|---|
| WO | WO 95/05384 | 2/1995 |
| WO | WO 97/05132 | 2/1997 |
| WO | WO 98/40370 | 9/1998 |

OTHER PUBLICATIONS

Rejesh, et al., *J. Chem. Res., Synop.*, 9, pp. 2062–2078 (1998).
Richard M. Keenan, et al., *Bioorganic & Medicinal Chemistry Letters*, 8 pp 3165–8170 (1998).
James Gilbart, et al.., *Antimicrobial Agents and Chemotherapy*, 37(1), pp 32–38 (1993).
Jacob J. Clement, et al., *Antimicrobial Agents and Chemotherapy*, 38(5), pp 1071–1078 (1994).
Susumu Takada, et al., *J. Medicinal Chemistry*, 39, pp 2844–2851 (1996).
Daniel Kern, et al., *Biochemi*, pp. 1257–1272 (1979).
Clegg, CA 105:24251 (1986).

*Primary Examiner*—D. Margaret Seaman
(74) *Attorney, Agent, or Firm*—James M. Hunter, Jr.; Mark R. Daniel

(57) ABSTRACT

Compounds, pharmaceutically acceptable salts, and compositions thereof of the general formula:

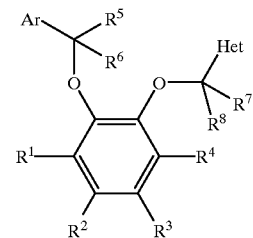

wherein Ar is aryl and heteroaryl; $R^1$, $R^2$, $R^3$, and $R^4$ are hydrido, alkyl, cyano, heteroaryl, hydroxy, amino, acylamino, halo, alkoxy, aryloxy, carboxyamido, alkenyl, cycloalkyl, heterocyclyl, acyl, acyloxy, carboalkoxy, carboxy, thio, sulfinyl, sulfonyl and sulfoxy, $R^5$, $R^6$, $R^7$, and $R^8$ are hydrido and lower alkyl; and Het is a nitrogen-containing heterocyclic ring.

8 Claims, No Drawings

CATECHOLS AS ANTIMICROBIAL AGENTS

RELATED APPLICATION

This application is a divisional of U.S. application Ser. No. 09/566,275, filed May 5, 2000, which claims the benefit of U.S. application Ser. No. 60/132,545, filed May 5, 1999.

FIELD OF THE INVENTION

This invention relates to the field of transfer ribonucleic acid (tRNA) synthetase inhibitors, their preparation and their use as antimicrobial agents.

BACKGROUND OF THE INVENTION

Aminoacyl tRNA synthetases (aaRS) are a family of essential enzymes that are found in virtually every biological cell and are responsible for maintaining the fidelity of protein synthesis. They specifically catalyze the aminoacylation of tRNA in a two step reaction:

amino acid (AA)+ATP=>AA-AMP+PPi

AA-AMP+tRNA=>tRNA-AA+AMP

The enzyme binds adenosine triphosphate (ATP) and its specific amino acid to catalyze formation of an aminoacyl adenylate complex (AA-AMP) with concomitant release of pyrophosphate (PPi). In the second step, the amino acid is transferred to the 2' or 3' terminus of the tRNA yielding "charged" tRNA and adenosine monophosphate (AMP). The charged tRNA delivers the amino acid to the nascent polypeptide chain on the ribosome.

There are at least twenty essential enzymes in this family for each organism. Inhibition of any of the essential tRNA synthetases disrupts protein translation, ultimately resulting in growth inhibition. Pseudomonic acid A, an antibacterial agent currently used in human therapy, provides clear evidence of the utility of tRNA synthetase inhibitors as useful pharmaceuticals. Pseudomonic acid A binds to one particular tRNA synthetase, isoleucyl tRNA synthetase, and inhibits isoleucyl adenylate formation in several Gram positive bacterial pathogens such as *Staphylococcus aureus,* resulting in the inhibition of protein synthesis, followed by growth inhibition.

Novel synthetic compounds that target tRNA synthetases offer clear advantages as useful therapeutic agents to curb the threat of drug resistance. Drug resistance allows a pathogen to circumvent the biochemical disruption caused by an antimicrobial agent. This resistance can be a result of a mutation that has been selected for and maintained. Pathogens in the environment have had repeated exposure to current therapeutics. This exposure has led to the selection of variant antimicrobial strains resistant to these drugs. Novel synthetic antimicrobial agents, therefore, would be expected to be useful to treat drug resistant pathogens, since the pathogen has never been exposed to the novel antimicrobial agent. The development of compounds or combinations of compounds targeting more than one tRNA synthetase is also advantageous. Accordingly, inhibition of more than one enzyme should reduce the incidence of resistance since multiple mutations in a pathogen would be required and are statistically rare.

SUMMARY OF THE INVENTION

The present invention discloses novel compounds which inhibit tRNA synthetases and have efficacy, including whole cell killing, against a broad spectrum of bacteria and fungi.

Described herein are compounds that exhibit tRNA synthetase inhibition.

The present invention comprises, in one aspect, compounds of Formula I.

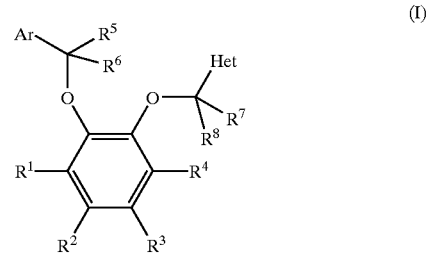

(I)

Group Ar of Formula I is selected from aryl or heteroaryl. Preferably, Ar is aryl, more preferably, substituted phenyl, even more preferably, 2,4-dichlorophenyl.

Each of substituents $R^1$, $R^2$, $R^3$, and $R^4$ of Formula I is independently hydrido, alkyl, cyano, heteroaryl, hydroxy, amino, acylamino, halo, alkoxy, aryloxy, carboxyamido, alkenyl, cycloalkyl, heterocyclyl, acyl, acyloxy, carboalkoxy, carboxy, thio, sulfinyl, sulfonyl or sulfoxy, provided that at least two of $R^1$, $R^2$, $R^3$ and $R^4$ is hydrido. Preferably, each of substituents $R^1$, $R^2$, $R^3$ and $R^4$ is independently selected from hydrido, carboxyl, alkyl, carboxyamido, N-acylaminosulfonyl, N-sulfonylcarboxyamido, and alkoxy. More preferably, each of substituents $R^1$, $R^2$, $R^3$ and $R^4$ is independently selected from —$(CH_2)_m CO_2 H$—, —$(CH_2)_m CONHCH(R^9)CO_2 H$—, —$CONHSO_2 R^{10}$—, and —$O(CH_2)_m CO_2 H$; wherein each of $R^9$ and $R^{10}$ is independently selected from alkyl and halo substituted alkyl; wherein m is selected from 0, 1 and 2.

Each of substituents $R^5$, $R^6$, $R^7$ and $R^8$ is independently hydrido or lower alkyl, preferably hydrido.

Group Het of Formula I is selected from

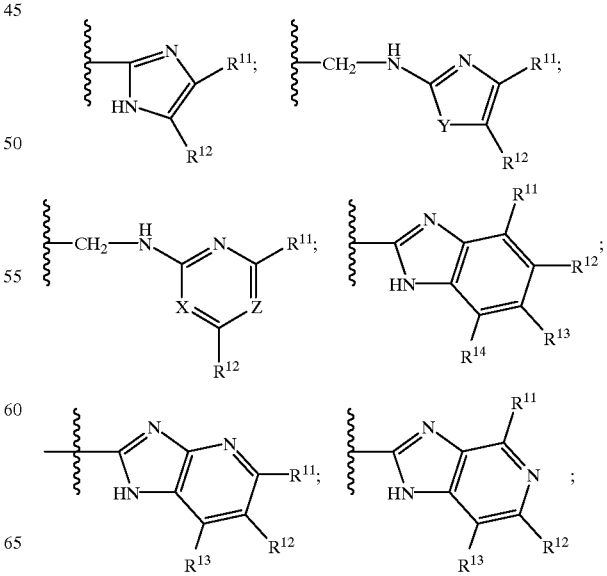

-continued

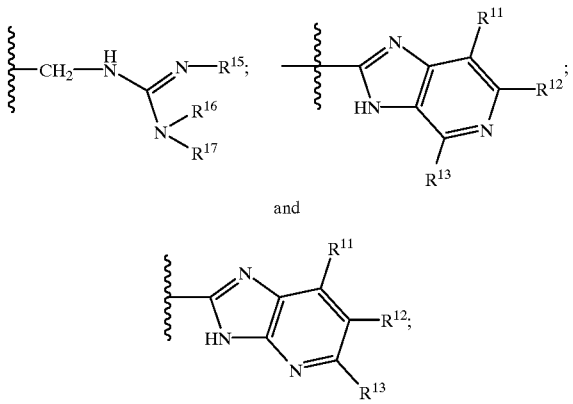

and

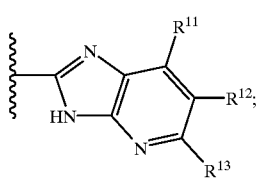

wherein X is selected from N or $CR^{11}$; wherein Y is selected from NH, S or O; wherein Z is selected from N or $CR^{12}$; wherein each of $R^{11}$, $R^{12}$, $R^{13}$, and $R^{14}$ is independently selected from nitro, halo, hydroxy, lower amino, lower alkyl, lower alkoxy, aryloxy, lower carboalkoxy, sulfinyl, sulfonyl, carboxy, lower thio, and sulfoxy; and wherein each of $R^{15}$, $R^{16}$, and $R^{17}$ is selected from hydrido, alkyl, aryl, nitro, amino, sulfonyl or sulfinyl. Preferably, Het is

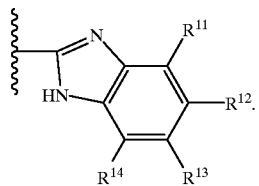

The invention also embraces pharmaceutically-acceptable salts of the forgoing compounds.

A further aspect of the invention comprises using a composition comprising the compound(s) of Formula I to inhibit a tRNA synthetase and in particular, to modulate the growth of bacterial or fungal organisms in mammals, a plant or a cell culture.

Yet another aspect of the invention involves a method of inhibiting the growth of microorganisms. The method involves exposing the microorganism to a compound of the invention, preferably a compound of Formula I, under conditions whereby a therapeutically effective amount of the compound enters the microorganism. The method is useful for inhibiting the growth of microrganisms in vivo and in vitro.

Another aspect of the invention is a pharmaceutical composition comprising the compound(s) of the invention and, in particular, the compounds of Formula I, useful in the treatment of microbial infections, e.g., bacterial infections, fungal infections. A related aspect of the invention is a method of making a medicament which involves placing a compound(s) of the invention, preferably a compound of Formula I, in a suitable pharmaceutically acceptable carrier.

These and other aspects of the invention will be more apparent in reference to the following detailed description of the invention.

DETAILED DESCRIPTION OF THE INVENTION

I. Definitions

Molecular terms, when used in this application, have their common meaning unless otherwise specified. The term "hydrido" denotes a single hydrogen atom (H). The term "acyl" is defined as a carbonyl radical attached to a hydrido, alkyl, alkenyl, alkynyl, cycloalkyl, heterocycyl, aryl or heteroaryl group, examples of such radicals being formyl, acetyl and benzoyl. The term "amino" denotes a nitrogen radical containing two substituents independently selected from the group consisting of hydrido, alkyl, cycloalkyl, heterocyclyl, aryl, and heteroaryl. Preferred amino radicals are $NH_2$ radicals and "lower amino" radicals, whereby the two substituents are independently selected from hydrido and lower alkyl. A subset of amino is "alkylamino", whereby the nitrogen radical contains at least 1 alkyl substituent. Preferred alkylamino groups contain alkyl groups that are substituted, for example, with a carboalkoxy group. The term "acyloxy" denotes an oxygen radical adjacent to an acyl group. The term "acylamino" denotes a nitrogen radical adjacent to an acyl, carboalkoxy or carboxyamido group. The term "carboalkoxy" is defined as a carbonyl radical adjacent to an alkoxy or aryloxy group. The term "carboxyamido" denotes a carbonyl radical adjacent to an amino group. A subset of carboxyamido is "N-sulfonylcarboxyamido" which denotes a carbonyl radical adjacent to an N-sulfonyl-substituted amino group. The term "halo" is defined as a bromo, chloro, fluoro or iodo radical. The term "thio" denotes a sulfur radical adjacent to a substituent group selected from hydrido, alkyl, cycloalkyl, heterocyclyl, aryl and heteroaryl, such as, methylthio and phenylthio. Preferred thio radicals are "lower thio" radicals containing lower alkyl groups.

The term "alkyl" is defined as a linear or branched, saturated radical having one to about ten carbon atoms unless otherwise specified. Preferred alkyl radicals are "lower alkyl" radicals having one to about five carbon atoms. One or more hydrogen atoms can also be replaced by a substitutent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, sulfinyl, sulfonyl, N-sulfonylcarboxyamido, and N-acylaminosulfonyl. Preferred substituents are carboalkoxy, carboxy, N-sulfonylcarboxyamido, and N-acylaminosulfonyl. Examples of alkyl groups include methyl, tert-butyl, isopropyl, methoxymethyl, carboxymethyl, and carbomethoxymethyl. The term "alkenyl" embraces linear or branched radicals having two to about twenty carbon atoms, preferably three to about ten carbon atoms, and containing at least one carbon—carbon double bond. One or more hydrogen atoms can also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, sulfinyl, sulfonyl, N-sulfonylcarboxyamido, and N-acylaminosulfonyl. Examples of alkenyl groups include ethylenyl or phenyl ethylenyl. The term "alkynyl" denotes linear or branched radicals having from two to about ten carbon atoms, and containing at least one carbon—carbon triple bond. One or more hydrogen atoms can also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, sulfinyl, sulfonyl, N-sulfonylcarboxyamido, and N-acylaminosulfonyl. Examples of alkynyl groups include propynyl. The term "aryl" denotes aromatic radicals in a single or fused carbocyclic ring system, having from five to twelve ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, sulfinyl, sulfonyl, N-sulfonylcarboxyamido, and N-acylaminosulfonyl. Examples of aryl groups include phenyl, 2,4-dichlorophenyl, naphthyl, biphenyl, terphenyl. "Heteroaryl" embraces aromatic radicals that contain one to four hetero atoms selected from oxygen, nitrogen and sulfur in a single or fused heterocyclic ring system, having from five to fifteen ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, sulfinyl, sulfonyl, N-sulfonylcarboxyamido, and N-acylaminosulfonyl. Examples of heteroaryl groups include, tetrazolyl, pyridinyl, thiazolyl, thiadiazoyl, isoquinolinyl, pyrazolyl, oxazolyl, oxadiazoyl, triazolyl, and pyrrolyl groups.

The term "cycloalkyl" is defined as a saturated or partially unsaturated carbocyclic ring in a single or fused carbocyclic ring system having from three to twelve ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, sulfinyl, sulfonyl, N-sulfonylcarboxyamido, and N-acylaminosulfonyl. Examples of a cycloalkyl group include cyclopropyl, cyclobutyl, cyclohexyl, and cycloheptyl. The term "heterocyclyl" embraces a saturated or partially unsaturated ring containing zero to four hetero atoms selected from oxygen, nitrogen and sulfur in a single or fused heterocyclic ring system having from three to twelve ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, sulfinyl, sulfonyl, N-sulfonylcarboxyamido, and N-acylaminosulfonyl. Examples of a heterocyclyl group include morpholinyl, piperidinyl, and pyrrolidinyl. The term "alkoxy" denotes oxy-containing radicals substituted with an alkyl, cycloalkyl or heterocyclyl group. Examples include methoxy, tert-butoxy, benzyloxy and cyclohexyloxy. Preferred alkoxy radicals are "lower alkoxy" radicals having a lower alkyl substituent. The term "aryloxy" denotes oxy-containing radicals substituted with an aryl or heteroaryl group. Examples include phenoxy. The term "sulfinyl" is defined as a tetravalent sulfur radical substituted with an oxo substituent and a second substituent selected from the group consisting of alkyl, cycloalkyl, heterocyclyl, aryl and heteroaryl. The term "sulfonyl" is defined as a hexavalent sulfur radical substituted with two oxo substituents and a third substituent selected from alkyl, cycloalkyl, heterocyclyl, aryl and heteroaryl. The term "N-acylaminosulfonyl" denotes a hexavalent sulfur atom bound to two oxo substituents and an N-acyl-substituted amino group.

The pharmaceutically-acceptable salts of the compounds of the invention (preferably a compound of Formula I) include acid addition salts and base addition salts. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of the compounds of the invention (preferably a compound of Formula I) may be prepared from an inorganic acid or an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically-acceptable base addition salts of compounds of the invention (preferably a compound of Formula I) include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine and procaine. All of these salts may be prepared by conventional means from the corresponding compound of the invention (preferably a compound of Formula I) by treating, for example, the compound of the invention (preferably a compound of Formula I) with the appropriate acid or base.

As used herein, "treating" means preventing the onset of, slowing the progression of, or eradicating the existence of the condition being treated, such as a microbial infection. Successful treatment is manifested by a reduction and, preferably, an eradication of the bacterial and/or fungal infection in the subject being treated.

The compounds of the invention (preferably compounds of Formula I) can possess one or more asymmetric carbon atoms and are thus capable of existing in the form of optical isomers as well as in the form of racemic or non-racemic mixtures thereof. The compounds of the invention (preferably compounds of Formula I) can be utilized in the present invention as a single isomer or as a mixture of stereochemical isomeric forms. Diastereoisomers can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of the invention (preferably compounds of Formula I) with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of the invention (preferably compounds of Formula I) can likewise be obtained by utilizing optically active starting materials. These isomers may be in the form of a free acid, a free base, an ester or a salt.

The invention also embraces isolated compounds. An isolated compound refers to a compound which represents at least 10%, preferably 20%, more preferably 50% and most preferably 80% of the compound present in the mixture, and exhibits a detectable (i.e. statistically significant) antimicrobial activity when tested in conventional biological assays such as those described herein.

II. Description

According to one aspect of the invention, compounds of Formula I are provided. The compounds are useful for inhibiting the enzymatic activity of a tRNA synthetase in vivo or in vitro. The compounds are particularly useful as antimicrobial agents, i. e., agents that inhibit the growth of bacteria or fungi.

One sub-class of compounds of Formula I are compounds of Formula II

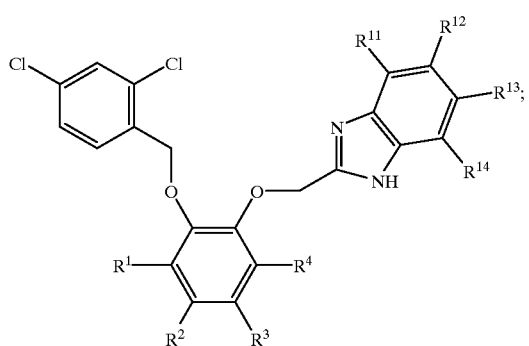

(II)

wherein substituents $R^1$, $R^2$, $R^3$, $R^4$ $R^{11}$, $R^{12}$, $R^{13}$, and $R^{14}$ are as previously described.

The compounds of the invention (preferably compounds of Formula I) are active against a variety of bacterial organisms. They are active against both Gram positive and Gram negative aerobic and anaerobic bacteria, including Staphylococci, for example *S. aureus;* Enterococci, for example *E. faecalis;* Streptococci, for example *S. pneumoniae;* Haemophilus, for example *H. influenza;* Moraxella, for example *M. catarrhalis;* and Escherichia, for example *E. coli*. The compounds of the present invention (preferably compounds of Formula I) are also active against Mycobacteria, for example *M. tuberculosis*. The compounds of the present invention (preferably compounds of Formula I) are also active against intercellular microbes, for example Chlamydia and Rickettsiae. The compounds of the present invention (preferably compounds of Formula I) are also active against Mycoplasma, for example *M. pneumoniae*.

The compounds of the present invention (preferably compounds of Formula I) are also active against fungal organisms, including, among other organisms, the species Aspergillus, Blastomyces, Candida, Coccidioides, Cryptococcus, Epidermophyton, Hendersonula, Histoplasma, Microsporum, Paecilomyces, Paracoccidioides, Pneumocystis, Trichophyton, and Trichosporium.

In a second aspect the invention provides a pharmaceutical composition comprising a compound of the invention, preferably a compound in accordance with the first aspect of the invention, and a pharmaceutically-acceptable carrier (described below). As used herein the phrase "therapeutically-effective amount" means that amount of a compound of the present invention (preferably a compound of Formula I) which prevents the onset of, alleviates the symptoms of, or stops the progression of a microbial infection. The term "microbial" means bacterial and fungal, for example a "microbial infection" means a bacterial or fungal infection. The term "treating" is defined as administering, to a subject, a therapeutically-effective amount of a compound of the invention (preferably a compound of Formula I). The term "subject", as described herein, is defined as a mammal, a plant or a cell culture.

According to another aspect of the invention, a method for inhibiting a tRNA synthetase is provided which comprises contacting a tRNA synthetase with a compound of the invention (preferably a compound of Formula I) under the conditions whereby the tRNA synthetase interacts with its substrates and its substrates react(s) to form an aminoacyl adenylate intermediate and, preferably, react(s) further to form a charged tRNA. Such conditions are known to those skilled in the art (see also e.g., the Examples for conditions), and PCT/US 96/11910, filed Jul. 18, 1996 (WO 97/05132, published Feb. 13, 1997), and U.S. Pat. No. 5,726,195. This method involves contacting a tRNA synthetase with an amount of compound of the invention (preferably a compound of Formula I) that is sufficient to result in detectable tRNA synthetase inhibition. This method can be performed on a tRNA synthetase that is contained within an organism or outside an organism.

In a further aspect, the invention provides a method for inhibiting the growth of microorganisms, preferably bacteria or fungi, comprising contacting said organisms with a compound of the invention (preferably a compound of Formula I) under conditions which permit entry of the compound into said organism and into said microorganism. Such conditions are known to one skilled in the art and are exemplified in the Examples. This method involves contacting a microbial cell with a therapeutically-effective amount of compound(s) of the invention (preferably compound(s) of Formula I), e.g. to inhibit cellular tRNA synthetase in vivo or in vitro. This method is used in vivo, for example, for treating microbial infections in mammals. Alternatively, the method is used in vitro, for example, to eliminate microbial contaminants in a cell culture, or in a plant.

In accordance with another aspect of the invention, the compositions disclosed herein are used for treating a subject afflicted by or susceptible to a microbial infection. The method involves administering to the subject a therapeutically effective amount of a compound of the invention (preferably a compound of Formula I). According to this aspect of the invention, the novel compositions disclosed herein are placed in a pharmaceutically acceptable carrier and are delivered to a recipient subject (preferably a human) in accordance with known methods of drug delivery. Exemplary procedures for delivering an antibacterial, antifungal and antimycoplasmal agent are described in U.S. Pat. No. 5,041,567, issued to Rogers and in PCT patent application number EP94/02552 (publication no. WO 95/05384), the entire contents of which documents are incorporated in their entirety herein by reference. In general, the methods of the invention for delivering the compositions of the invention in vivo utilize art-recognized protocols for delivering the agent with the only substantial procedural modification being the substitution of the compounds of the invention (preferably compounds of Formula I) for the drugs in the art-recognized protocols. Likewise, the methods for using the claimed composition for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the invention (preferably compounds of Formula I) for the agents used in the art-recognized protocols.

The pharmaceutical preparations disclosed herein are prepared in accordance with standard procedures and are administered at dosages that are selected to reduce, prevent or eliminate the infection (See, e.g., Remington's Pharmaceutical Sciences, Mack Publishing Company, Easton, Pa. and Goodman and Gilman's The Pharmaceutical Basis of Therapeutics, Pergamon Press, New York, N.Y., the contents of which are incorporated herein by reference, for a general description of the methods for administering various antimicrobial agents for human therapy). The compositions of the invention (preferably of Formula I) can be delivered using controlled (e.g., capsules) or sustained release delivery systems (e.g., bioerodable matrices). Exemplary delayed release delivery systems for drug delivery that are suitable for administration of the compositions of the invention (preferably of Formula I) are described in U.S. Pat. Nos. 4,452,775 (issued to Kent), 5,239,660 (issued to Leonard), 3,854,480 (issued to Zaffaroni).

The pharmaceutically-acceptable compositions of the present invention comprise one or more compounds of the invention (preferably compounds of Formula I) in association with one or more nontoxic, pharmaceutically-acceptable carriers and/or diluents and/or adjuvants and/or excipients, collectively referred to herein as "carrier" materials, and if desired other active ingredients.

The compounds of the present invention (preferably compounds of Formula I) are administered by any route, preferably in the form of a pharmaceutical composition adapted to such a route, as illustrated below and are dependent on the condition being treated. The compounds and compositions can be, for example, administered orally, intravascularly, intraperitoneally, subcutaneously, intramuscularly or topically.

For oral administration, the pharmaceutical compositions are in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maizestarch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

The pharmaceutical compositions can be administered via injection. Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For topical use the compounds of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compounds of the present invention can be in powder form for reconstitution in the appropriate pharmaceutically acceptable carrier at the time of delivery.

The dosage regimen for treating an infection with the compound and/or compositions of this invention is selected in accordance with a variety of factors, including the type, age, weight, sex and medical condition of the patient, the severity of the infection, the route and frequency of administration and the particular compound employed. In general, dosages are determined in accordance with standard practice for optimizing the correct dosage for treating an infection.

The compositions can contain from 0.1% to 99% by weight, preferably 10–60% by weight, of the active ingredient, depending on the method of administration. If the compositions contain dosage units, each dosage unit preferably contains from 50–500 mg of the active material. For adult human treatment, the dosage employed preferably ranges from 100 mg to 3 g, per day, depending on the route and frequency of administration.

If administered as part of a total dietary intake, the amount of compound employed can be less than 1% by weight of the diet and preferably no more than 0.5% by weight. The diet for animals can be normal foodstuffs to which the compound can be added or it can be added to a premix.

Further references to features and aspects of the invention are provided in the Examples set out hereafter.

EXAMPLES

The following Examples are detailed descriptions of the methods of preparation of compounds of Formula I. These detailed preparations fall within the scope of, and serve to exemplify, the invention. These Examples are presented for illustrative purposes only and are not intended as a limitation on the scope of the invention.

Scheme I
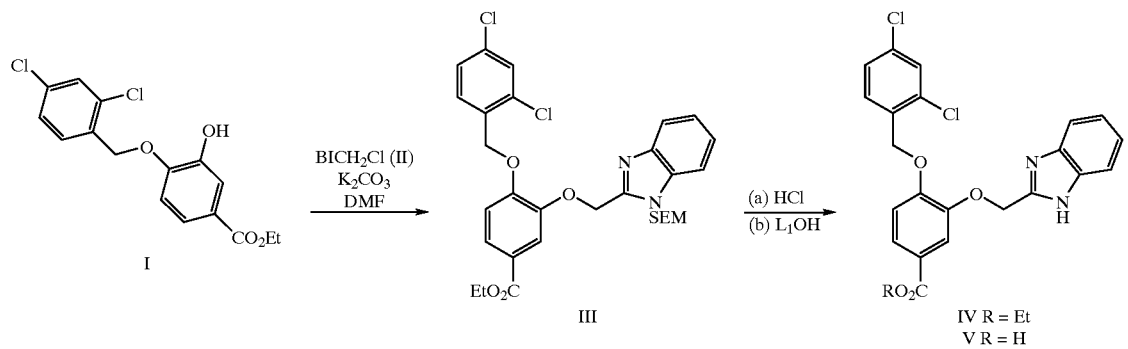
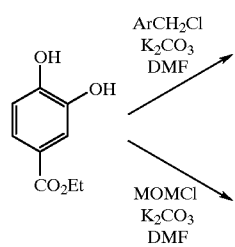
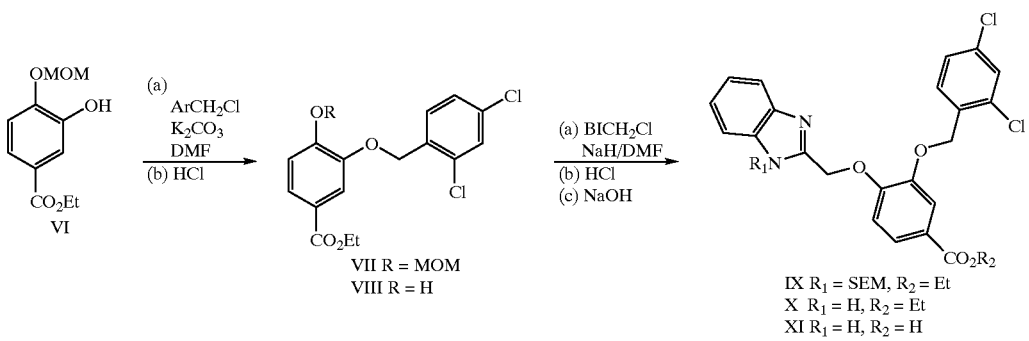
Scheme II
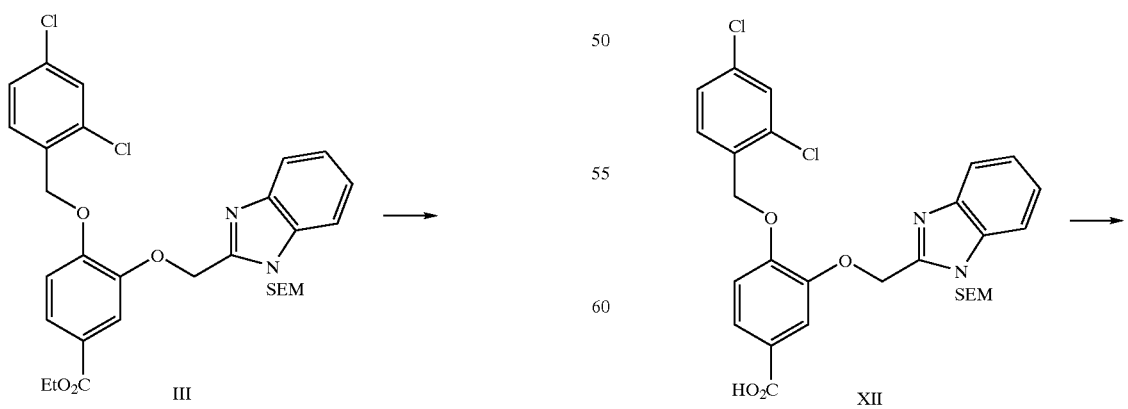

-continued

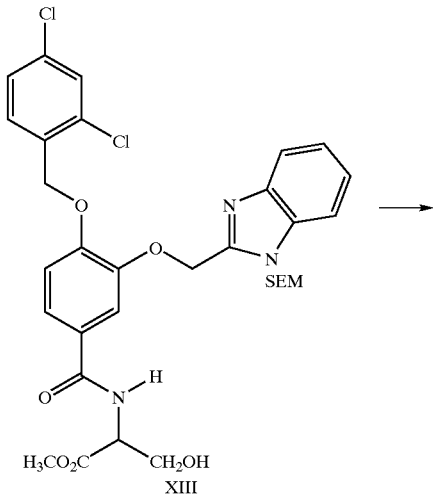
XIII

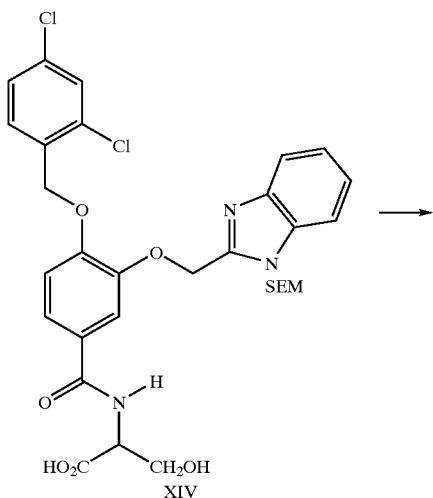
XIV

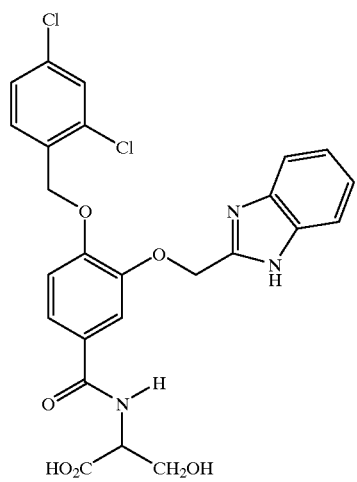
XV

Synthesis of I

A solution of 5.0 g ethyl-3,4-dihydroxybenzoate, 3.8 ml 2,4-dichlorobenzylchloride and 7.58 g potassium carbonate in 50 ml anhydrous N,N-dimethylformamide was stirred at room temperature for 24 hours before partitioning with 500 ml ethyl acetate and 500 ml brine. The organic layer was dried with 10 g sodium sulfate and concentrated. Purification by silica gel chromatography using 5–20% ethyl acetate in hexanes afforded 1.0 g of I.

Synthesis of II 3.0 g of 2-chloromethylbenzimidazole and 3.0 ml trimethylsilyl ethoxymethyl chloride was added to a solution of 6 ml triethylamine in 20 ml dichloromethane. The reaction stirred at room temperature for 24 hours before partitioning with 250 ml ethyl acetate and 2×200 ml brine. The organic layer was dried with 5 g magnesium sulfate and concentrated. Purification by silica gel chromatography using 20% ethyl acetate in hexanes gave 1.23 g of II as a while solid.

Synthesis of III

A solution of 115 mg I, 100 mg II and 250 mg potassium carbonate in 5 ml anhydrous N,N'-Dimethylformamide was stirred at room temperature for 24 hours before partitioning with 100 ml ethyl acetate and 100 ml brine. The organic layer was dried with 5 g sodium sulfate and concentrated to give 199 mg of III as a colorless oil.

Synthesis of IV

To a solution of 199 mg III in 5 ml dioxane was added 0.2. ml concentrated hydrochloric acid. The reaction was heated at 100° C. for 2 hours before partitioning with 50 ml ethyl acetate and 50 ml saturated solution of sodium bicarbonate. The organic layer was dried with 2 g magnesium sulfate and concentrated. Purification by silica gel chromatography using 40% ethyl acetate in hexanes gave 135 mg of IV as a white solid.

Synthesis of V

A solution of 130 mg IV and 200 mg lithium hydroxide in 2 ml water and 4 ml tetrahydrofuran was stirred at room temperature for 48 hours. The reaction was diluted with 20 ml water and 1 N hydrochloric acid added to adjust the pH to 7. The precipitate was filtered to give 77 mg of V.

Synthesis of VI

To 1.0 g ethyl 3,4-dihydroxybenzoate, 5.0 g potassium carbonate in 30 ml anhydrous N,N'-dimethylformamide was added 0.42 ml methoxymethylchloride. The reaction was stirred at room temperature for 24 hours before partitioning with 100 ml ethylacetate and 2×100 ml brine. The organic layer was dried with 5 g magnesium sulfate and concentrated. Purification by silica gel chromatography using 10% ethyl acetate in hexanes afforded 0.41 g of VI as a colorless oil.

Synthesis of VII

A solution of 410 mg VI, 0.38 ml 2,4-dichlorobenzylchloride and 500 mg potassium carbonate in 10 ml anhydrous N,N-dimethylformamide was stirred at room temperature for 24 hours before partitioning with 100 ml ethyl acetate and 100 ml brine. The organic layer was dried with 5 g magnesium sulfate and concentrated to give 0.5 g of VII as a colorless oil.

Synthesis of VIII

To a solution of 0.5 g VII in 10 ml methanol was added 0.3 ml concentrate hydrochloric acid. The resulting solution was heated at reflux for 1 hour before partitioning with 100 ml ethyl acetate and 100 ml brine. The organic layer was dried with magnesium sulfate and concentrated. The resulting solid was recrystallized from the ethyl acetate and hexanes to give 0.43 g of VIII as a white solid.

Synthesis of IX 250 mg of VIII was added to a stirring suspension of 29 mg 60% sodium hydride in mineral oil in 8 ml anhydrous N,N-dimethylformamide. After 10 minutes, 217 mg II was added to the reaction. The reaction was allowed to stir at room temperature for 24 hours before partitioning between 100 ml ethyl acetate and 100 ml brine. The organic layer was dried with 2 g magnesium sulfate and concentrated. Purification by silica gel chromatography using 20% ethyl acetate in hexanes gave 325 mg of IX as a colorless oil.

Synthesis of X

A solution of 0.32 g IX in 0.4 ml concentrated hydrochloric acid and 10 ml 1.4-dioxane was heated at 100° C. for 2 hours before partitioning with 50 ml ethyl acetate and 50 ml saturated solution of sodium bicarbonate. The organic layer was dried with 2 g magnesium sulfate and concentrated. Purification by silica gel chromatography using 40% ethyl acetate in hexanes afforded 0.21 g of X as a white solid.

Synthesis of XI

A solution of 0.19 g X in 8 ml tetrahydrofuran and 5 ml 6 N sodium hydroxide was stirred at room temperature for 24 hours. After evaporation of the tetrahydrofuran, the reaction was acidified with 1N HCl to pH=4. The resulting white precipitate was filtered and washed with 2×10 ml water. Purification by silica gel chromatography using 10% methanol in dichloromethane afforded 40 mg XI.

Synthesis of XII

A solution of 3.53 g III in 10 ml 6 N sodium hydroxide, 20 ml methanol and 20 ml 1,4-dioxane was stirred at room temperature for 2 hours before partitioning with 200 ml ethyl acetate and 200 ml 1 N hydrochloric acid. The organic layer was dried with 10 g sodium sulfate and concentrated. The solid was triturated with ether and filtered to give 2.9 g of XII as a white solid.

Synthesis of XIII

To a mixture of 0.29 g XII, 0.6 ml diisopropylethylamine and 0.12 g L-serine methylester in 10 ml anhydrous N,N'dimetylformamide was added 0.15 g 1-(3-dimethylaminopropyl)-3-ethylcarbodiimide hydrochloride. The reaction was stirred at room temperature for 24 hours before partitioning with 50 ml ethyl acetate and 50 ml hydrochloric acid. The organic layer was washed with 50 ml brine and dried with 2 g sodium sulfate. Purification by silica gel chromatography using 10% methanol in dichloromethane gave 0.10 g of XIII.

Synthesis of XIV

A solution of 0.10 g XIII in 2 ml 6 N NaOH, 5 ml methanol and 5 ml 1,4-dioxane was stirred at room temperature for 2 hours before adding 4 ml 4 N HCl. The reaction was partitioned with 30 ml ethyl acetate and 30 ml brine. The organic layer was dried with 1 g sodium sulfate and concentrated to afford 0.08 g of XIV.

Synthesis of XV

A solution of 0.08 g XIV in 5 ml and 0.5 ml tetrabutylamimonium fluoride in tetrahydrofuran was refluxed for 4 hours before partitioning with 20 ml ethyl acetate and 2×20 ml brine. The organic layer was dried with 1 g sodium sulfate and concentrated. Purification by silica gel chromatogrphy using 10% methanol in dichloromethane yielded 20 mg of XV as a white solid.

Scheme III

Synthesis XVI:
Rink Amide-AM 4-O-Allyl-3, 4-Dihydroxybenzamide Resin

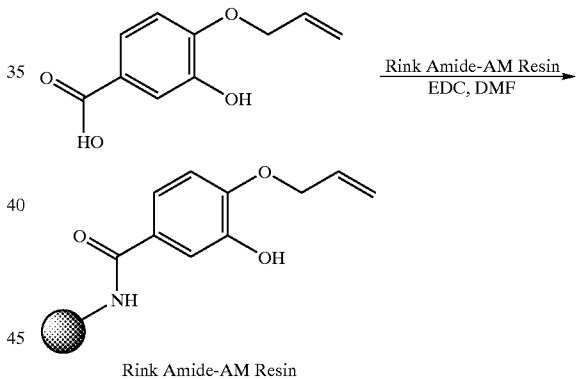

A sample of 1.00 g of Rink Amide-AM resin (Novabiochem, loads 0.65 mmol/g) was treated with 15 ml of 20% piperidine in DMF for 10 minutes to remove the Fmoc protecting group, and was then washed 5 times with DMF. To the resin was added 15 ml of DMF, 400 mg of 4-O-allyl-3,4-dihydroxybenzoic acid (3 eq.) and 400 mg of EDC (3 eq.). The mixture was rotated overnight in a reaction tube, then the resin was drained and washed five times with DMF, five times with MeOH, five times with $CH_2Cl_2$, then dried under high vacuum to a mass of 3.04 g. To measure loading, 100 mg of the resin was cleaved with 95% trifluoroacetic acid in methylene chloride and produced 14 mg of 4-O-allyl-3,4-dihydroxybenzamide (MS 194, M+1), indicating 100% loading.

Synthesis XVII:
Resin Synthesis of 4-O-(2-Benzimidazolyl) Methyl-3-O-(2,4-Dichlorobenzyl)-3,4-Dihydrobenzamide by Mitsunobu followed by Alkylation

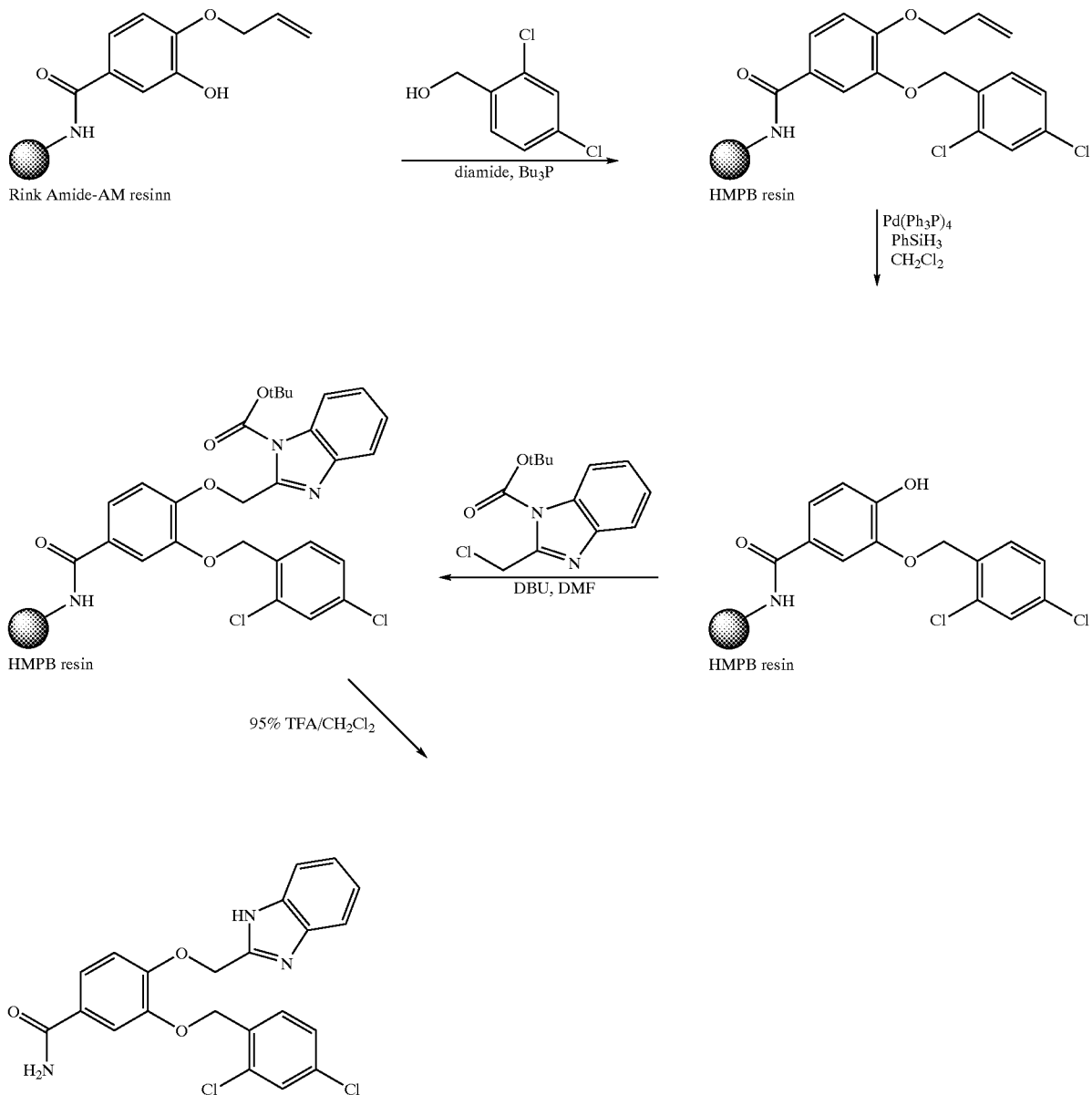

To 0.175 g of Rink amide-AM 4-O-allyl-3,4-dihydroxybenzamide resin (loads 0.65 mmol/g) was added 1.5 ml of distilled THF, 0.310 g of 2,4-dichlorobenzyl alcohol (5 eq.), 0.297 ml of Bu₃P (5 eq.), and finally 200 mg of diamide (5 eq.). The mixture was rotated for 5 hrs in a reaction tube, then the resin was drained and washed five times with DMP, five times with CH$_2$Cl$_2$, then dried under high vacuum. The resin was swelled in 1.5 ml CH$_2$Cl$_2$, and to it was added 0.200 ml of PhSiH$_3$ (ca. 20 eq.) and 15 mg of Pd(Ph$_3$P)$_4$ (ca. 0.1 eq.) The mixture was rotated overnight in a reaction tube, then the resin was drained and washed five times with DMF, five times with CH$_2$Cl$_2$, then dried under high vacuum. This material was swelled in 2.0 ml DMF, and to it was added 89 mg of 1-t-Boc-2-chloromethylbenzimidazole (3 eq.) and 0.050 ml of DBU (3 eq.) The mixture was rotated overnight in a reaction tube, then the resin was drained and washed five times with DMF, five times with CH$_2$Cl$_2$, and then cleaved by treating it with 2 ml of 95% trifluoroacetic acid in methylene chloride for 45 minutes. The cleavage solution was drained and the solvent was removed under a nitrogen stream. The residue was purified by HPLC on a YMC-PACK ODS 100×20 mm column, eluting at 20 ml/min on a gradient, beginning with 90/10 water/CH$_3$CN (0.1% TFA) and ramping up linearly to straight acetonitrile (0.1% TFA) over an 11 minute run. The fractions containing the product were combined and reduced in volume under a stream of nitrogen, then lyophilized to yield 24 mg of a white, fluffy solid which was analyzed by LC mass spec (409 M+1).

Synthesis XVIII:
Resin Synthesis of 4-O-(2-Benzimidazolyl) Methyl-3-O-(2-Fluoro-4-Bromobenzyl)-3,4-Dihydrobenzamide by Tandem Alkylation

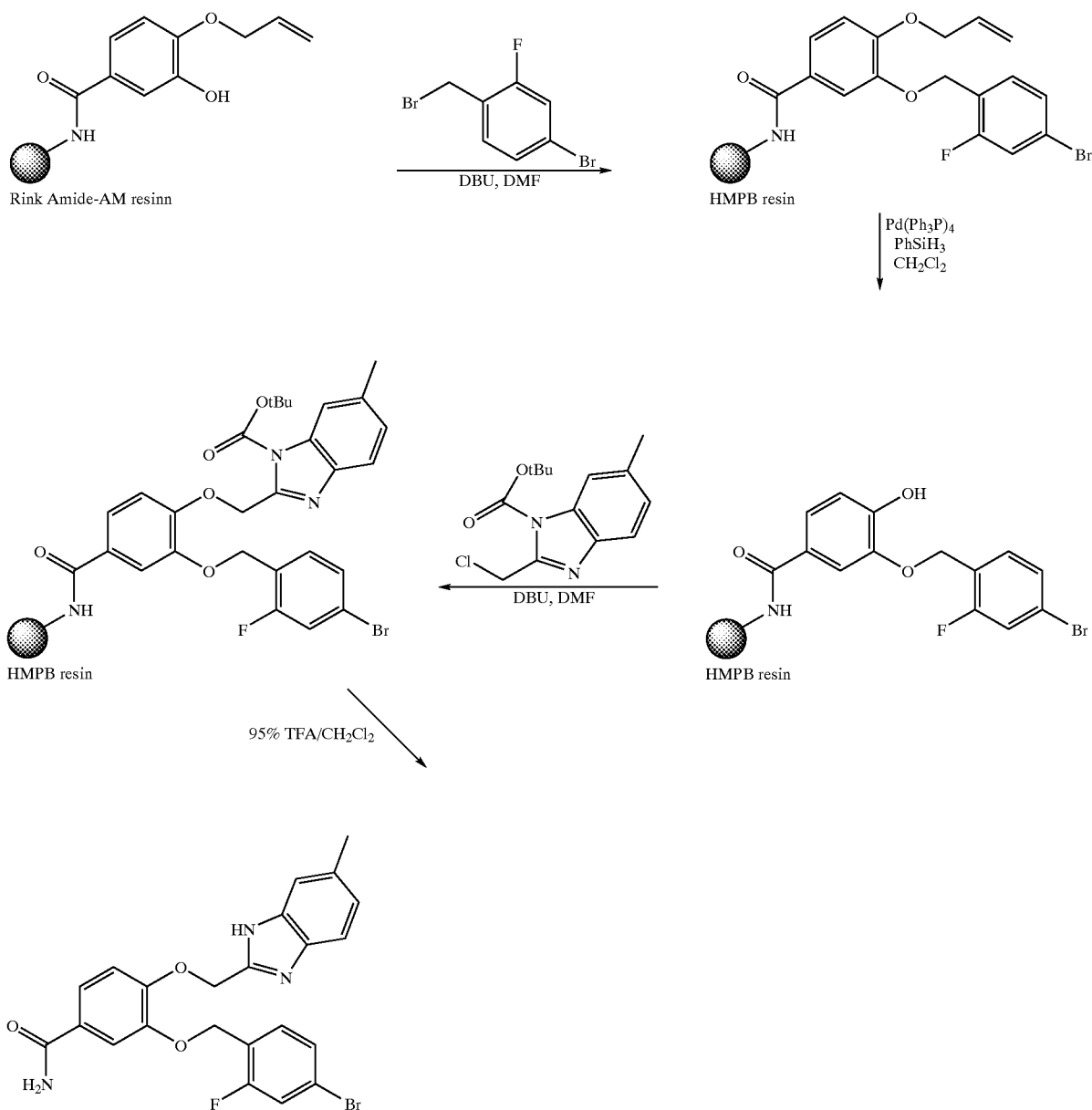

To 0.175 g of Rink amide-AM 4-O-allyl-3,4-dihydroxybenzamide resin (loads 0.65 mmol/g) was added 1.5 ml of sieve dried DMF, 0.154 g of 2-fluoro-4-bromobenzyl bromide (5 eq.), 0.085 ml diazabicycloundecane (DBU, 1.55 mmol, 5 eq.). The mixture was rotated for 5 hrs in a reaction tube, then the resin was drained and washed five times with DMF, five times with $CH_2Cl_2$, then dried under high vacuum. The resin was swelled in 1.5 ml $CH_2Cl_2$, and to it was added 0.200 ml of $PhSiH_3$ (ca. 20 eq.) and 15 mg of $Pd(Ph_3P)_4$ (ca. 0.1 eq.) The mixture was rotated overnight in a reaction tube, then the resin was drained and washed five times with DMF, five times with $CH_2Cl_2$, then dried under high vacuum. This material was swelled in 2.0 ml DMF, and to it was added 89 mg of 1-t-Boc-2-chloromethyl-6-methylbenzimidazole (3 eq.) and 0.050 ml of DBU (3 eq.) The mixture was rotated overnight in a reaction tube, then the resin was drained and washed five times with DMF, five times with CH2Cl2, and then cleaved by treating it with 2 ml of 95% trifluoroacetic acid in methylene chloride for 45 minutes. The cleavage solution was drained and the solvent was removed under a nitrogen stream. The residue was purified by HPLC on a YMC-PACK ODS 100×20 mm column, eluting at 20 ml/min on a gradient, beginning with 90/10 water/CH3CN (0.1% TFA) and ramping up linearly to straight acetonitrile (0.1% TFA) over an 11 minute run. The fractions containing the product were combined and reduced in volume under a stream of nitrogen, then lyophilized to yield 24 mg of a white, fluffy solid which was analyzed by LC mass spec (409 M+1).

The carboxamides prepared according to this scheme are presented below in Table 1:

TABLE 1

Carboxamides Prepared from Rink Amide-AM
4-O-allyl-3,4-dihydroxybenzamide Resin

| Cmpd | Reagent 1 | Reagent 2 | Structure of Product | Mass Spec |
|---|---|---|---|---|
| 1 | | | | 484 |
| 2 | | | | 456 |
| 3 | | | | 466 |
| 4 | | | | 442 |

TABLE 1-continued
Carboxamides Prepared from Rink Amide-AM
4-O-allyl-3,4-dihydroxybenzamide Resin
| Cmpd | Reagent 1 | Reagent 2 | Structure of Product | Mass Spec |
|---|---|---|---|---|
| 5 | 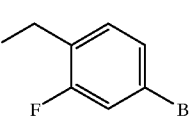 | 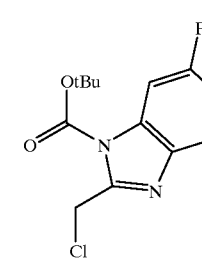 | 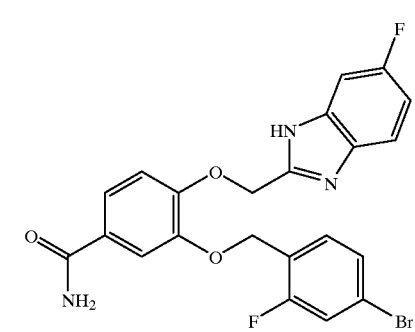 | 488 |
| 6 | 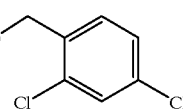 | 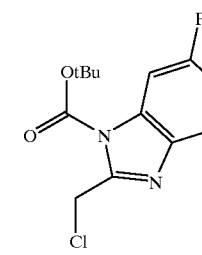 | 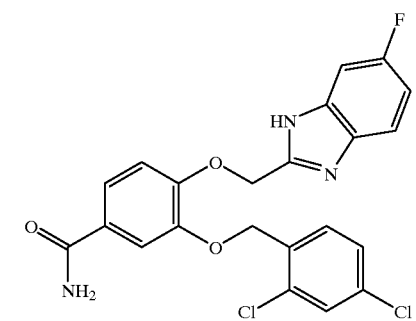 | 460 |
| 7 | 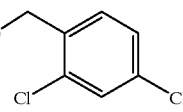 | 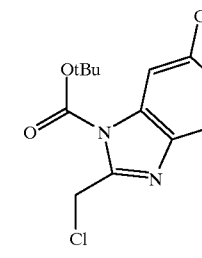 | 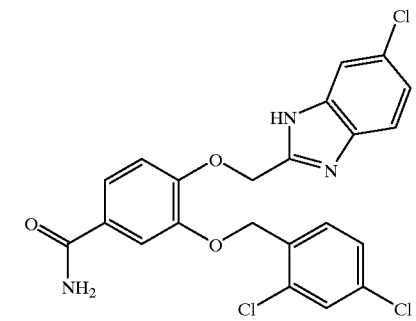 | 476 |
| 8 | 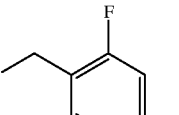 | 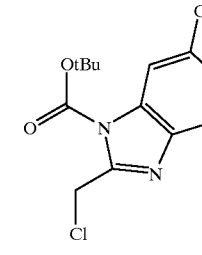 | 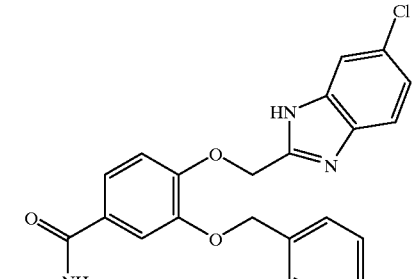 | 504 |

TABLE 1-continued
Carboxamides Prepared from Rink Amide-AM
4-O-allyl-3,4-dihydroxybenzamide Resin
| Cmpd | Reagent 1 | Reagent 2 | Structure of Product | Mass Spec |
|---|---|---|---|---|
| 9 | 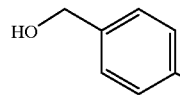 | 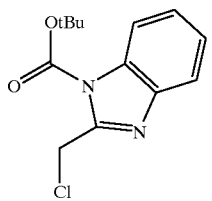 | 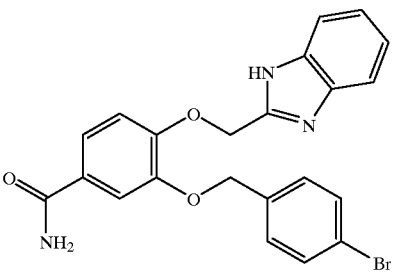 | 452 |
| 10 | 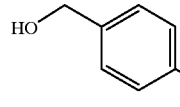 | 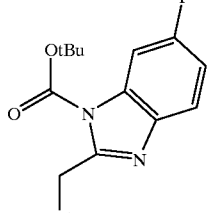 | 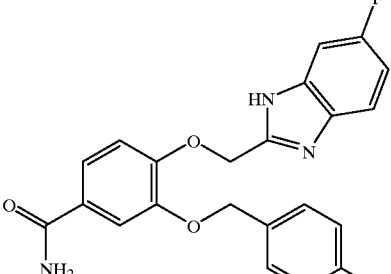 | 470 |
| 11 | 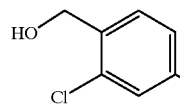 |  | 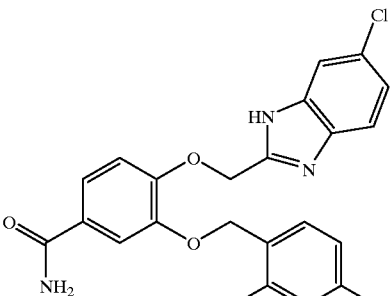 | 476 |
| 12 | 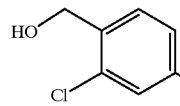 | 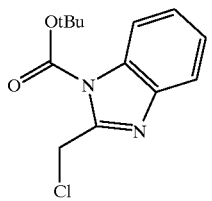 | 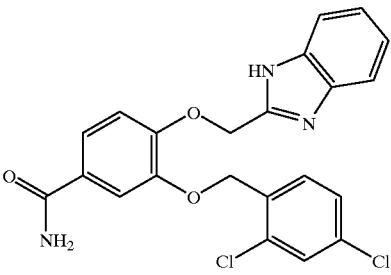 | 442 |

Scheme IV

Synthesis XIX:
Ethyl 4-O-Allyl-3, 4-Dihydroxybenzoate

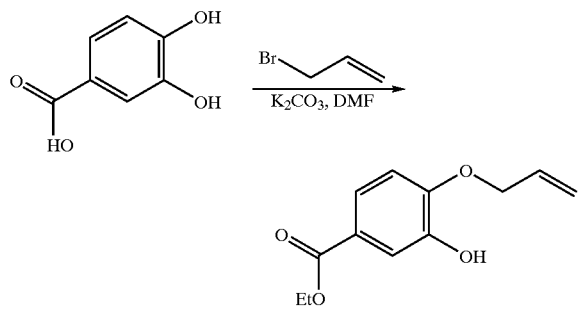

To 5.46 g (30 mmol) of ethyl 3,4-dihydroxybenzote was added 20 ml sieve-dried DMF, 2.58 ml of allyl bromide (30 mmol), and finally 2.07 g (15 mmol) potassium carbonate. The mixture was stirred overnight at room temperature, at which point the temperature was elevated to 55° C. and stirring was continued for four hours. Analysis by TLC eluting with 9:1 hexane/ethyl acetate showed starting material near the baseline, the desired monoalkylated product and its isomer as two very close spots at ca. Rf 0.5 with the desired isomer major and lower Rf, and finally the dialkylated side product at ca. Rf 0.8. The reaction mixture was concentrated to a thick paste on the rotary evaporator, then partitioned between 500 ml of EtOAc and 200 ml of 1 N HCl. The organic layer was separated and washed with 100 ml of 1N HCl, 100 ml of water, 100 ml of brine, then dried over MgSO$_4$ and filtered. The solvent was removed on the rotary evaporaor to provide a dark, yellow oil. This material was chromatographed on silica (column dimensions: 14" length×2" diameter). Initially the column was eluted with 95:5 hexane/EtOAc until the dialkylated side product came off, then elution was carried on with 90:10 hexane/EtOAc ramping up to 85:15 hexane/EtOAc after most of the unwanted monoalkylated isomer eluted. Fractions were concentrated to provide the desired compound, ethyl 4-O-allyl-3,4-dihydroxybenzoate, as a white amorphous solid (2.86 g). Also isolated was 785 mg of the isomer, ethyl 3-O-allyl-3,4-dihydroxybenzoate and 990 mg of a mixture of the two isomers.

Note that the NMR of the 2 monoalkylated isomers are almost identical, except for the position of the phenolic proton, which is farther up-field in the desired 4-O-allyl isomer.

Ethyl 4-O-Allyl-3,4-dihydroxybenzoate (major, desired product):

1H NMR (500 MHz, acetone-d6): δ 7.99 (s, 1H phenolic proton), 7.51 (d, 1H), 7.49 (s, 1H), 6.93 (d, 1H), 6.1 (m, 1H), 5.45 (d, 1H), 5.25 (d, 1H), 4.71 (d, 2H), 4.28 (q, 2H), 1.25 (t, 3H). MS (ESI): 223 (M+H+)

Ethyl 3-O-Allyl-3,4-dihydroxybenzoate (minor, undesired product):

1H NMR (500 MHz, acetone-d6): δ 8.43 (s, 1H phenolic proton), 7.58 (m, 2H), 7.03 (d, 1H), 6.1 (m, 1H), 5.45 (d, 1H), 5.25 (d, 1H), 4.71 (d, 2H), 4.28 (q, 2H), 1.25 (t, 3H). MS (ESI): 223 (M+H+)

Synthesis XX:
Ethyl 4-O-Allyl-3-O-(2,4-Dichlorobenzyl)-3,4-Dihydroxybenzoate

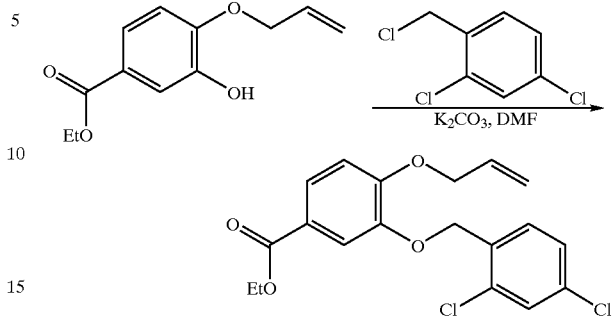

To 3.74 g (16.8 mmol) of ethyl 4-O-allyl-3,4-dihydroxybenzote was added 25 ml sieve-dried DMF, 2.8 ml of 2,4-dichlorobenzyl chloride (20 mmol, 1.2 eq.), and finally 2.8 g (20 mmol, 1.2 eq.) of potassium carbonate. The mixture was stirred overnight at room temperature, after which analysis by TLC eluting with 1:1 hexane/ethyl acetate showed complete conversion to product. The reaction mixture was concentrated to a thick paste on the rotary evaporator, then partitioned between 500 ml of EtOAc and 200 ml of 1 N HCl. The organic layer was separated and washed with 100 ml of 1N HCl, 100 ml of water, 100 ml of brine, then dried over MgSO$_4$ and filtered. The crude oil thus obtained was carried on to the next step without purification.

Synthesis XXI:
Ethyl 3-O-(2,4-Dichlorobenzyl)-3,4-Dihydroxybenzoate

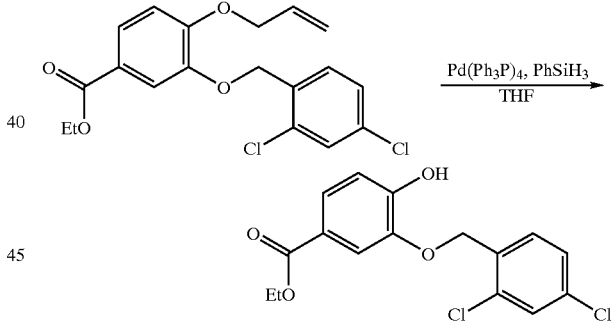

To the crude product of the previous reaction was added 40 ml of sieve dried methylene chloride, 25.0 ml of phenylsilane (201 mmol, 12 eq.), and finally 2.3 g of Pd(Ph$_3$P)$_4$. The mixture was stirred for 4 hours at room temperature, after which analysis by TLC eluting with 1:1 hexane/ethyl acetate showed complete conversion to product. The reaction mixture was concentrated on the rotary evaporator and chromatographed directly on silica, eluting with 10% EtOAc in hexane. Fractions were concentrated to provide the desired compound, ethyl 3-O-(2,4-dichlorobenzyl)-3,4-dihydroxybenzoate, as a white amorphous solid (4.56 g, 13.4 mmol, 80% for two steps).

Ethyl 3-O-(2,4-dichlorobenzyl)-3,4-dihydroxybenzoate

1H NMR (500 MHz, acetone-d6): δ 8.65 (s, 1H phenolic proton), 7.74 (d, 1H), 7.66 (s, 1H), 7.61 (d, 1H), 7.59 (s, 1H), 7.44 (d, 1H), 6.98 (d, 1H), 5.28 (s, 2H), 4.28 (q, 2H), 1.32 (t, 3H). MS (ESI): 341 (M+H+)

Synthesis XXII:
1-t-Boc-2-Chloromethylbenzimidazole

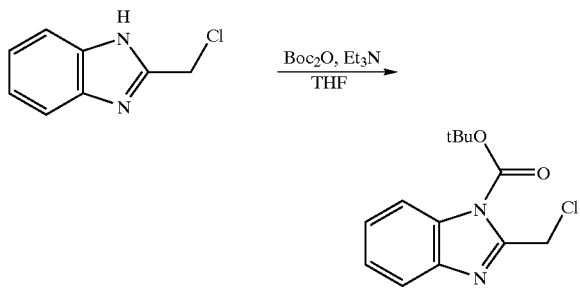

To 4.0 g (24 mmol) of ethyl 2-chloromethylbenzimidazole was added 40 ml of distilled THF, 7.86 g of t-boc anhydride (36 mmol, 1.5 eq.), 5.0 ml of Et$_3$N (36 mmol, 1.5 eq.), and finally 2.93 g of dimethylaminopyridine (24 mmol, 1 eq.). The mixture was stirred at room temperature for 3 hrs., after which time the reaction was diluted with 300 ml of EtOAc and extracted with 100 ml of 1N HCl, 100 ml of water, 100 ml of brine, then dried over MgSO$_4$ and filtered. The solvent was removed on the rotary evaporator to provide a dark, yellow oil. This material was chromatographed on silica eluting with 90:10 hexane/EtOAc. Fractions were concentrated to provide the desired compound, 1-t-boc-2-chloromethylbenzimidazole as a pale, yellow oil (4.06 g, 63%).

Synthesis XXIII:
Ethyl 4-O-(2-(1-t-Boc-Benzimidazolyl)) Methyl-3-O-(2,4-Dichlorobenzyl)-3,4-Dihydroxybenzoate

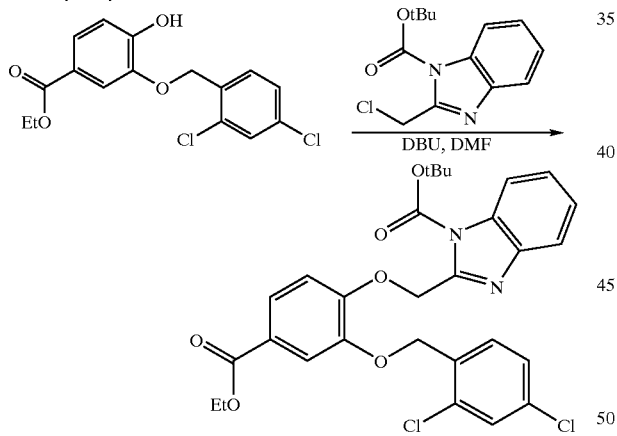

To 4.30 g (12.6 mmol) of ethyl 3-O-(2,4-dichlorobenzyl)-3,4-dihydroxybenzoate was added 20 ml of sieve-dried DMF, 4.03 g of 1-t-boc-2-chloromethylbenzimidazole (15.1 mmol, 1.2 eq.), and finally 2.26 ml of diazabicycloundecane (DBU, 15.1 mmol, 1.2 eq.). The mixture was stirred overnight at room temperature, at which time analysis by TLC eluting with 9:1 hexane/ethyl acetate showed complete reaction. The reaction mixture was concentrated to a thick paste on the rotary evaporator, then chromatographed directly on silica using an elution gradient of 10% increasing to 20% ethyl acetate in hexane. Fractions were concentrated to provide the desired compound, ethyl 4-O-(2-(1-t-boc-benzimidazolyl))methyl-3-O-(2,4-dichlorobenzyl)-3,4-dihydroxybenzoate, as a white amorphous solid (5.48 g, 9.58 mmol, 76%).

Synthesis XXIV:
4-O-(2-Benzimidazolyl)Methyl-3-O-(2,4-Dichlorobenzyl)-3,4-Dihydroxybenzoic Acid

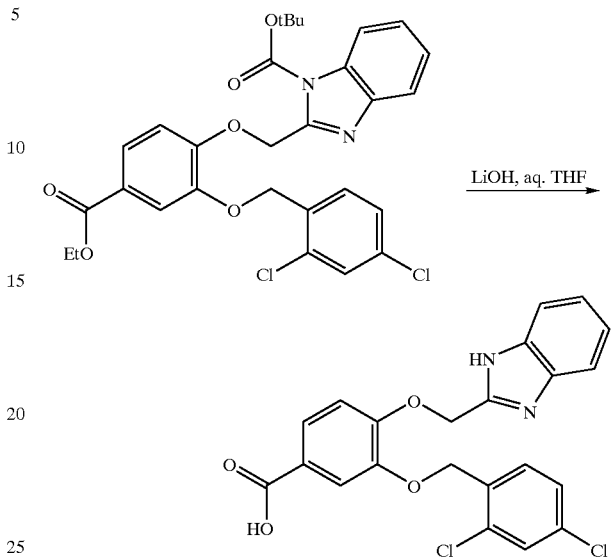

To 5.48 g (9.58 mmol) of ethyl 4-O-(2-(1-t-boc-benzimidazolyl))methyl-3-O-(2,4-dichlorobenzyl)-3,4-dihydroxybenzoate was added 70 ml of 1:1 THF/water and 2.0 g of LiOH—H$_2$O. The mixture was stirred overnight at 40° C., then neutralized with 1N HCl. Product precipitated and was collected by filtration and dried under high vacuum to yield 4.2 g of a white, amorphous solid sufficiently pure for subsequent reactions.

Synthesis XXV:
Modular Synthesis Of Amides Of 4-O-(2-Benzimidazolyl)Methyl-3-O-(2,4-Dichlorobenzyl)-3,4-Dihydroxybenzoic Acid

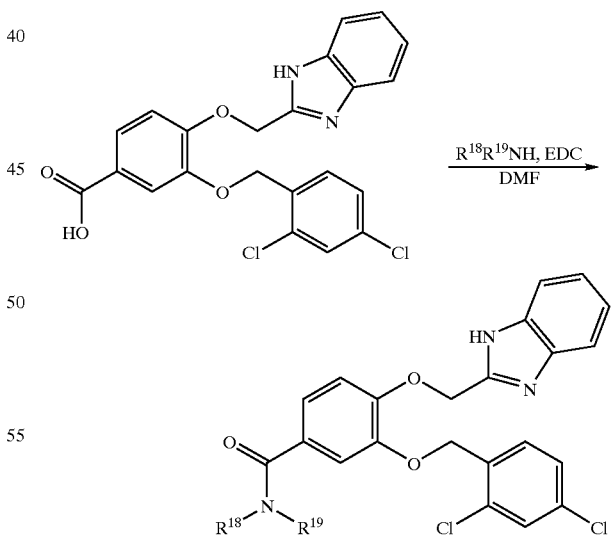

These modular amidation reactions are normally done 20 to 40 at a time by weighing the primary or secondary amines into vials, then adding to each stock solutions of catechol starting material and EDC/HOBt.

First, 0.3–0.6 mmol of each amine was weighed into a separate vial. Allowing a two-fold variation in mass has no deleterious effect on the reaction and considerably speeds the weighing, which is the slowest and most laborious part of the sequence. Liquid amines were introduced based on volume (0.4 mmol), using microliter syringes. Stock Solution A was made by dissolving 4-O-(2-Benzimidazolyl)methyl-3-O-(2,4-dichlorobenzyl)-3,4-dihydroxybenzoic Acid in DMF to a concentration of 32 mg/ml. To each vial was added 0.25 ml (8 mg, 1.8 mmol of catechol) of Stock Solution A. Stock Solution B was made by adding DMF to 132 mg of EDC and 93 mg of HOBt to a 5 ml solution volume. To each vial was added 0.25 ml (8 mg, 1.8 mmol of catechol) of Stock Solution B. In cases where the amine was a hydrochloride or other acid salt, 0.006 ml of $Et_3N$ was added for each mole of acid (e.g., a diammonium dichloride would require 0.012 ml). Vials in which solid remained were then warmed briefly with a heat gun and sonicated. In most cases this resulted in a homogeneous solution, but not always, and it was discovered that a homogeneous solution was not always necessary for a reaction to work. All vials were stirred overnight at room temperature, after which time 1 ml of water and 1 ml of saturated sodium bicarbonate solution were introduced to each vial. This mix was extracted with 3×1 ml of ethyl acetate for each vial, which was combined in a test tube, and the solvent was evaporated under a nitrogen stream. The resulting solid was dissolved in 1 ml of DMSO (with warming if necessary) and purified by HPLC on a YMC-PACK ODS 100×20 mm column, eluting at 20 ml/min on a gradient, beginning with 90/10 water/$CH_3CN$ (0.1% TFA) and ramping up linearly to straight acetonitrile (01% TFA) over an 11 minute run. The fractions containing the product were combined and reduced in volume under a stream of nitrogen, the lyophilized to provide as product as a fluffy solid. Yields were typically 5 to 10 mg. Table 2 provides amides that were prepared in accordance with Scheme III (each was characterized by LCMS):

TABLE 2

Modular Synthesis of 4-O-(2-Benzimidazolyl)methyl-3-O-(2,4-dichlorobenzyl)-3,4-dihydroxybenzoic Acid

| Cmpd. | Amine | Product | Mass Spec |
|---|---|---|---|
| 13 | | | 717 |
| 14 | | | 589 |
| 15 | | | 611 |

TABLE 2-continued

Modular Synthesis of 4-O-(2-Benzimidazolyl)methyl-3-O-(2,4-dichlorobenzyl)-3,4-dihydroxybenzoic Acid

| Cmpd. | Amine | Product | Mass Spec |
|---|---|---|---|
| 16 | | | 530 |
| 17 | | | 618 |
| 18 | | | 598 |

TABLE 2-continued

Modular Synthesis of 4-O-(2-Benzimidazolyl)methyl-3-O-(2,4-dichlorobenzyl)-3,4-dihydroxybenzoic Acid

| Cmpd. | Amine | Product | Mass Spec |
|---|---|---|---|
| 19 | (structure) | (structure) | 498 |
| 20 | (structure) | (structure) | 612 |
| 21 | (structure) | (structure) | 556 | deprotect by treatment with 50% TFA/CH2Cl2 for 10 min before HPLC

TABLE 2-continued

Modular Synthesis of 4-O-(2-Benzimidazolyl)methyl-3-O-(2,4-dichlorobenzyl)-3,4-dihydroxybenzoic Acid

| Cmpd. | Amine | Product | Mass Spec |
|---|---|---|---|
| 22 | | | 626 |
| 23 | | | 570 |
| 24 | | deprotect by treatment with 50% TFA/CH2Cl2 for 10 min before HPLC | 585 |

TABLE 2-continued

Modular Synthesis of 4-O-(2-Benzimidazolyl)methyl-3-O-(2,4-dichlorobenzyl)-3,4-dihydroxybenzoic Acid

| Cmpd. | Amine | Product | Mass Spec |
|---|---|---|---|
| 25 | (methyl tryptophan ester) | (benzimidazolylmethyl/dichlorobenzyl-dihydroxybenzamide-tryptophan methyl ester) | 642 |
| 26 | (methyl threonine ester) | (benzimidazolylmethyl/dichlorobenzyl-dihydroxybenzamide-threonine methyl ester) | 599 |
| 27 | TBDMSO—NH$_2$ | (benzimidazolylmethyl/dichlorobenzyl-dihydroxybenzohydroxamic acid) | 457 deprotect by treatment with 50% TFA/CH2Cl2 for 10 min before HPLC |

TABLE 2-continued

Modular Synthesis of 4-O-(2-Benzimidazolyl)methyl-3-O-(2,4-dichlorobenzyl)-3,4-dihydroxybenzoic Acid

| Cmpd. | Amine | Product | Mass Spec |
|---|---|---|---|
| 28 | (structure) | (structure) | 549 |
| 29 | (structure) | (structure) | 535 |
| 30 | (structure) | (structure) | 597 |

TABLE 2-continued

Modular Synthesis of 4-O-(2-Benzimidazolyl)methyl-3-O-(2,4-dichlorobenzyl)-3,4-dihydroxybenzoic Acid

| Cmpd. | Amine | Product | Mass Spec |
|---|---|---|---|
| 31 | (alanine amide) | | 512 |
| 32 | (1-(3-aminopropyl)-2-pyrrolidinone) | | 556 |
| 33 | (serine amide) | | 599 |

TABLE 2-continued

Modular Synthesis of 4-O-(2-Benzimidazolyl)methyl-3-O-(2,4-dichlorobenzyl)-3,4-dihydroxybenzoic Acid

| Cmpd. | Amine | Product | Mass Spec |
|---|---|---|---|
| 34 | | | 526 |
| 35 | | | 568 |
| 36 | | | 512 |

TABLE 2-continued
Modular Synthesis of 4-O-(2-Benzimidazolyl)methyl-3-O-(2,4-dichlorobenzyl)-3,4-dihydroxybenzoic Acid
| Cmpd. | Amine | Product | Mass Spec |
|---|---|---|---|
| 37 | 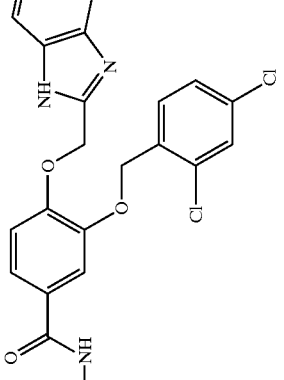 |  | 554 |
| 38 |  | 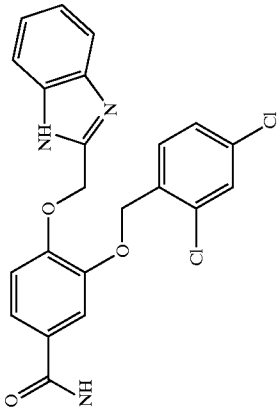 | 552 |
| 39 | 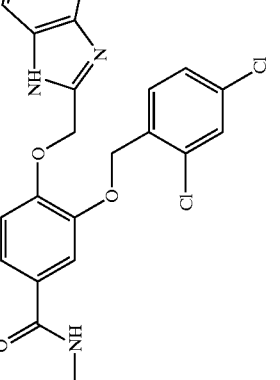 |  | 554 |

TABLE 2-continued

Modular Synthesis of 4-O-(2-Benzimidazolyl)methyl-3-O-(2,4-dichlorobenzyl)-3,4-dihydroxybenzoic Acid

| Cmpd. | Amine | Product | Mass Spec |
|---|---|---|---|
| 40 | furfurylamine structure | product structure | 521 |
| 41 | tetrahydrofurfurylamine structure | product structure | 525 |
| 42 | histidinol structure | product structure | 565 |

TABLE 2-continued

Modular Synthesis of 4-O-(2-Benzimidazolyl)methyl-3-O-(2,4-dichlorobenzyl)-3,4-dihydroxybenzoic Acid

| Cmpd. | Amine | Product | Mass Spec |
|---|---|---|---|
| 43 | cyclopropylmethylamine | | 495 |
| 44 | (2-aminoethyl)trimethylammonium triflate | | 527 |
| 45 | benzylamine | | 531 |

TABLE 2-continued
Modular Synthesis of 4-O-(2-Benzimidazolyl)methyl-3-O-(2,4-dichlorobenzyl)-3,4-dihydroxybenzoic Acid
| Cmpd. | Amine | Product | Mass Spec |
|---|---|---|---|
| 46 | 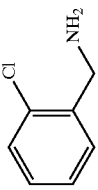 | 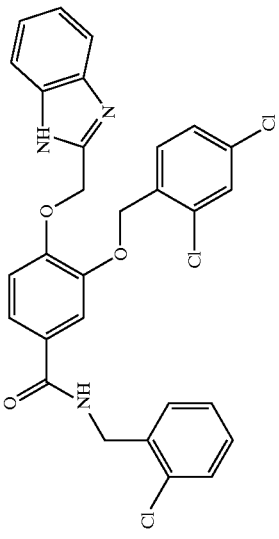 | 565 |
| 47 |  | 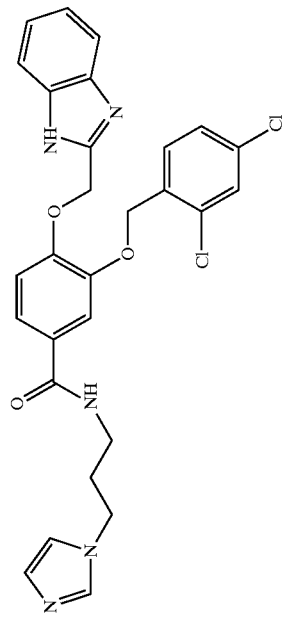 | 549 |
| 48 | 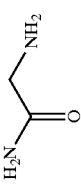 | 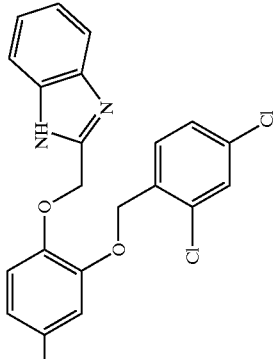 | 498 |

TABLE 2-continued

Modular Synthesis of 4-O-(2-Benzimidazolyl)methyl-3-O-(2,4-dichlorobenzyl)-3,4-dihydroxybenzoic Acid

| Cmpd. | Amine | Product | Mass Spec |
|---|---|---|---|
| 49 | | | 546 |
| 50 | | | 558 |
| 51 | | | 580 |

Scheme V

Synthesis XXVI:
Ethyl 4-O-Allyl-3,4-Dihydroxybenzoate

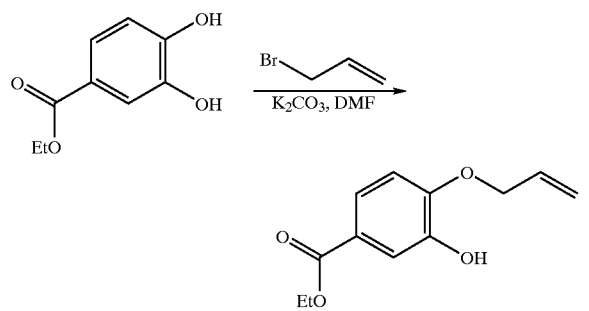

To 5.46 g (30 mmol) of ethyl 3,4-dihydroxybenzoate was added 20 ml sieve-dried DMF, 2.58 ml of allyl bromide (30 mmol), and finally 2.07 g (15 mmol) potassium carbonate. The mixture was stirred overnight at room temperature, at which point the temperature was elevated to 55° C. and stirring was continued for 4 hours. Analysis by TLC eluting with 9:1 hexane/ethyl acetate showed starting material near the baseline, the desired monoalkylated product and its isomer as two very close spots at ca. Rf 0.5 with the desired isomer major and lower Rf, and finally the dialkylated side product at ca. Rf 0.8. The reaction mixture was concentrated to a thick paste on the rotary evaporator, then partitioned between 500 ml of EtOAc and 200 ml of 1 N HCl. The organic layer was separated and washed with 100 ml of 1N HCl, 100 ml of water, 100 ml of brine, then dried over MgSO$_4$ and filtered. The solvent was removed on the rotary evaporator to provide a dark, yellow oil. This material was chromatographed on silica (column dimensions: 14" length× 2" diameter). Initially the column was eluted with 95:5 hexane/EtOAc until the dialkylated side product came off, then elution was carried on with 90:10 hexane/EtOAc ramping up to 85:15 hexane/EtOAc after most of the unwanted monoalkylated isomer eluted. Fractions were concentrated to provide the desired compound, ethyl 4-O-allyl-3,4-dihydroxybenzoate, as a white amorphous solid (2.86 g). Also isolated was 785 mg of the isomer, ethyl 3-O-allyl-3,4-dihydroxybenzoate and 990 mg of a mixture of the two isomers.

Note that the NMR of the two monoalkylated isomers are almost identical, except for the position of the phenolic proton, which is farther up-field in the desired 4-O-allyl isomer.

Ethyl 4-O-Allyl-3,4-dihydroxybenzoate (major, desired product):

1H NMR (500 MHz, acetone-d6): δ 7.99 (s, 1H phenolic proton), 7.51 (d, 1H), 7.49 (s, 1H), 6.93 (d, 1H), 6.1 (m, 1H), 5.45 (d, 1H), 5.25 (d, 1H), 4.71 (d, 2H), 4.28 (q, 2H), 1.25 (t, 3H). MS (ESI): 223 (M+H+)

Ethyl 3-O-Allyl-3,4-dihydroxybenzoate (minor, undesired product)::

1H NMR (500 MHz, acetone-d6): δ 8.43 (s, 1H phenolic proton), 7.58 (m, 2H), 7.03 (d, 1H), 6.1 (m, 1H), 5.45 (d, 1H), 5.25 (d, 1H), 4.71 (d, 2H), 4.28 (q, 2H), 1.25 (t, 3H). MS (ESI): 223 (M+H+)

Synthesis XXVII:
4-O-Allyl-3,4-Dihydroxybenzoic Acid

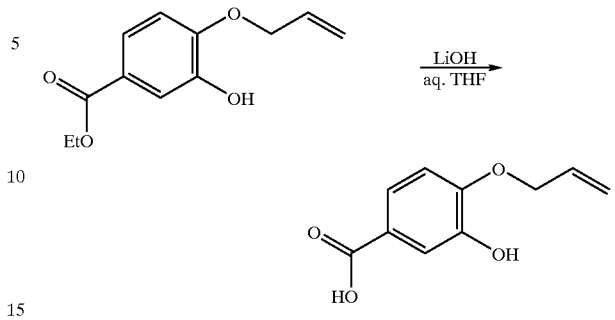

To 1.00 g (4.50 mmol) of ethyl 4-O-allyl-3,4-dihydroxybenzoate was added 10 ml 1:1 THF/water, 378 mg of LiOH—H$_2$O (9.00 mmol, 2.0 eq.), and finally 2.8 g (20 mmol, 1.2 eq.) of potassium carbonate. The mixture was stirred overnight at room temperature, after which analysis by TLC eluting with 5:1 hexane/ethyl acetate incomplete conversion to product. An additional 150 mg of LiOH—H$_2$O (0.4 eq.) was added and stirring was continued for another 24 hours, after which time the reaction was judged to be complete by TLC. The reaction mixture was diluted with 100 ml of water and extracted once with 25 ml of EtOAc and once with 25 ml of CH$_2$Cl$_2$. The aqueous layer was acidified to pH=1 with 1N HCl, then extracted twice with 25 ml of EtOAc then twice with 25 ml of CH$_2$Cl$_2$. These organics were combined, dried over MgSO$_4$, and filtered. The solvent was removed on the rotary evaporator and the resulting amorphous white solid was dried under high vacuum to provide 835 mg (96%) of crude product of sufficient purity to use in further reactions.

4-O-Allyl-3,4-dihydroxybenzoic Acid:

1H NMR (500 MHz, DMSO-d6): δ 7.37 (d, 1H), 7.36 (s, 1H), 6.97 (d, 1H), 6.05 (m, 1H), 5.40 (d, 1H), 5.25 (d, 1H), 4.60 (d, 2H). MS (ESI): 195 (M+H+)

Synthesis XXVIII
HMPB 4-O-Allyl-3,4-Dihydroxybenzoate Resin

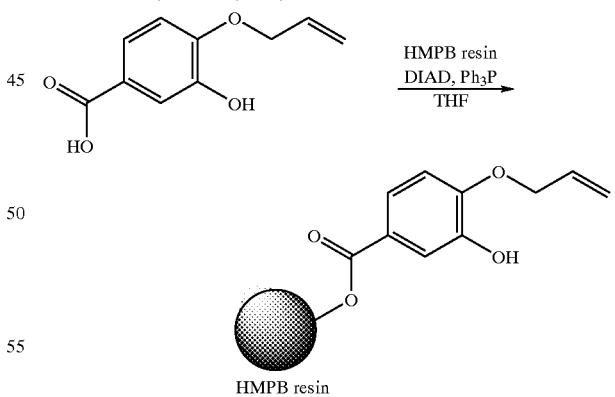

To 2.65 g of HMPB resin (Novobiochem, loads 0.51 mmol/g, 1.35 mmol) was added 50 ml of distilled THF, 0.655 g of 4-O-allyl-3,4-dihydroxybenzoic acid (3.38 mmol, 2.5 eq.), 900 mg of Ph$_3$P (3.38 mmol, 2.5 eq.), and finally 0.675 ml of diisopropyldiazodicarboxylate (3.38 mmol, 2.5 eq.). The mixture was rotated overnight in a reaction tube, then the resin was drained and washed five times with DMF, five times with MeOH, five times with CH$_2$Cl$_2$, then dried under high vacuum to a mass of 3.04 g. To measure loading, 100 mg of the resin was cleaved with 10% trifluoroacetic acid in methylene chloride and produced 5.0 mg of 4-O-allyl-3,4-dihydroxybenzoic acid of excellent purity, indicating 58% loading.

4-O-Allyl-3,4-dihydroxybenzoic Acid:
1H NMR (500 MHz, DMSO-d6): δ 7.37 (d, 1H), 7.36 (s, 1H), 6.97 (d, 1H), 6.05 (m, 1H), 5.40 (d, 1H), 5.25 (d, 1H), 4.60 (d, 2H) MS (ESI): 195 (M+H+)

Synthesis XXIX
Resin Synthesis of 4-O-(2-Benzimidazolyl)Methyl-3-O-(2-Fluoro-4-Bromobenzyl)-3,4-Dihydroxybenzoic Acid by Tandem Alkylation

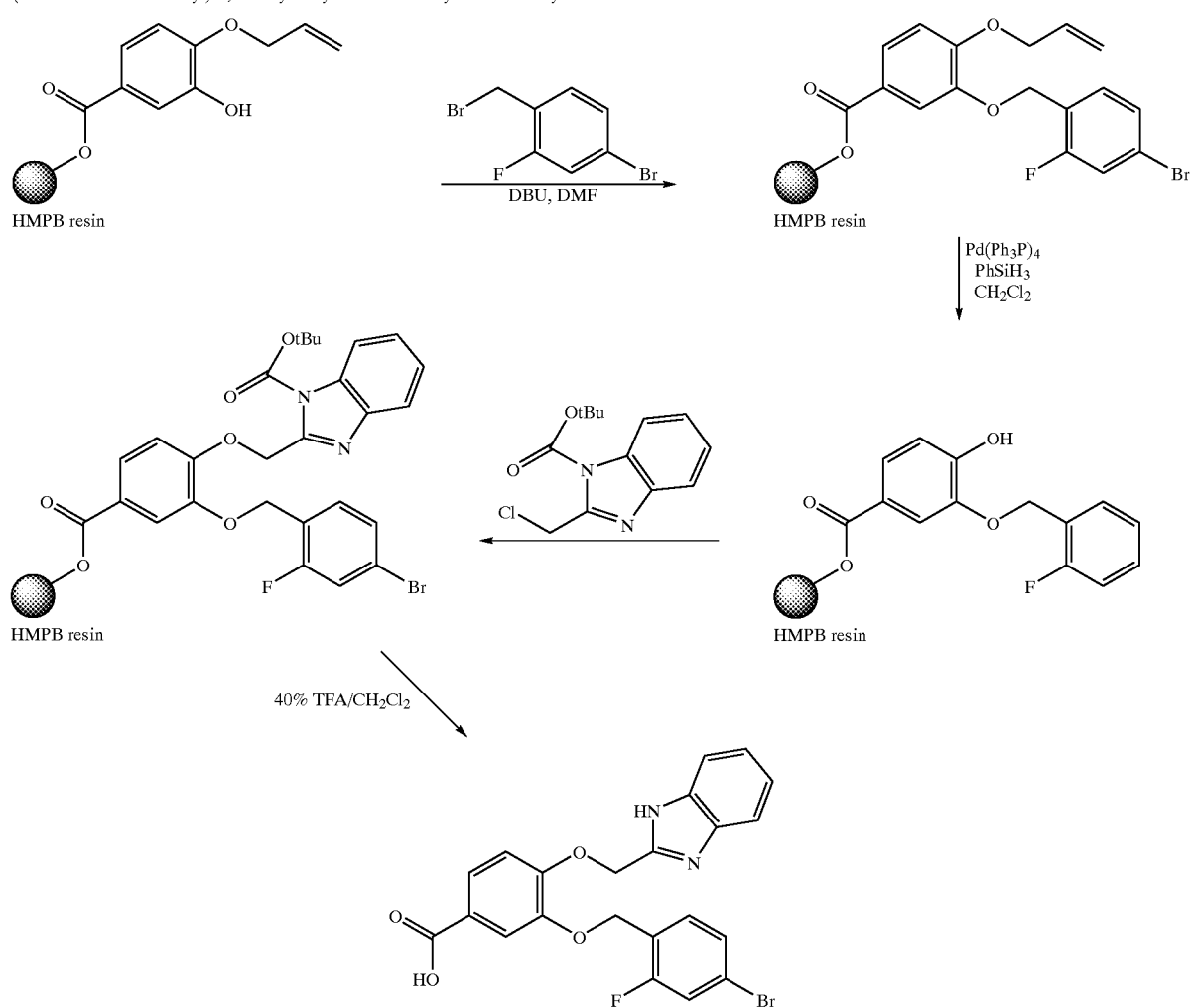

To 0.600 g of HMPB 4-O-allyl-3,4-dihydroxybenzoate resin (loads 0.51 mmol/g) was added 5 ml of sieve-dried DMF, 0.415 g of 2-fluoro-4-bromobenzyl bromide (1.55 mmol, 5 eq.), 0.231 ml of diazabicycloundecane (DBU, 1.55 mmol, 5 eq.). The mixture was rotated overnight in a reaction tube, then the resin was drained and washed five times with DMF, five times with CH$_2$Cl$_2$, then dried under high vacuum. The resin was swelled in 3 ml CH$_2$Cl$_2$, and to it was added 0.500 ml of PhSiH$_3$ (13 eq.) and 40 mg of Pd(Ph$_3$P)$_4$ (0.1 eq.) The mixture was rotated overnight in a reaction tube, then the resin was drained and washed five times with DMF, five times with CH$_2$Cl$_2$, then dried under high vacuum to a mass of 530 mg. A sample of 180 mg of this material was swelled in 2.0 ml DMF, and to it was added 73 mg of 1-t-Boc-2-chloromethylbenzimidazole (3 eq.) and 0.041 ml of DBU (3 eq.) The mixture was rotated overnight in a reaction tube, then the resin was drained and washed five times with DMF, five times with CH$_2$Cl$_2$, and then cleaved by treating it with 2 ml of 40% trifluoroacetic acid in methylene chloride for 30 minutes. The cleavage solution was drained and the solvent was removed under a nitrogen stream. The residue was purified by HPLC on a YMC-PACK ODS 100×20 mm column, eluting at 20 ml/min on a gradient, beginning with 90/10 water/CH$_3$CN (0.1% TFA) and ramping up linearly to straight acetonitrile (01% TFA) over an 11 minute run. The fractions containing the product were combined and reduced in volume under a stream of nitrogen, then lyophilized to yield 10 mg of a white, fluffy solid which was analyzed by LC mass spec (471 M+1).

Synthesis XXX
Resin Synthesis of 4-O-(2-Benzimidazolyl)methyl-3-O-
(4-chlorobenzil)-3,4-dihydroxybenzioc Acid by Mitsunobu followed by Alkylation

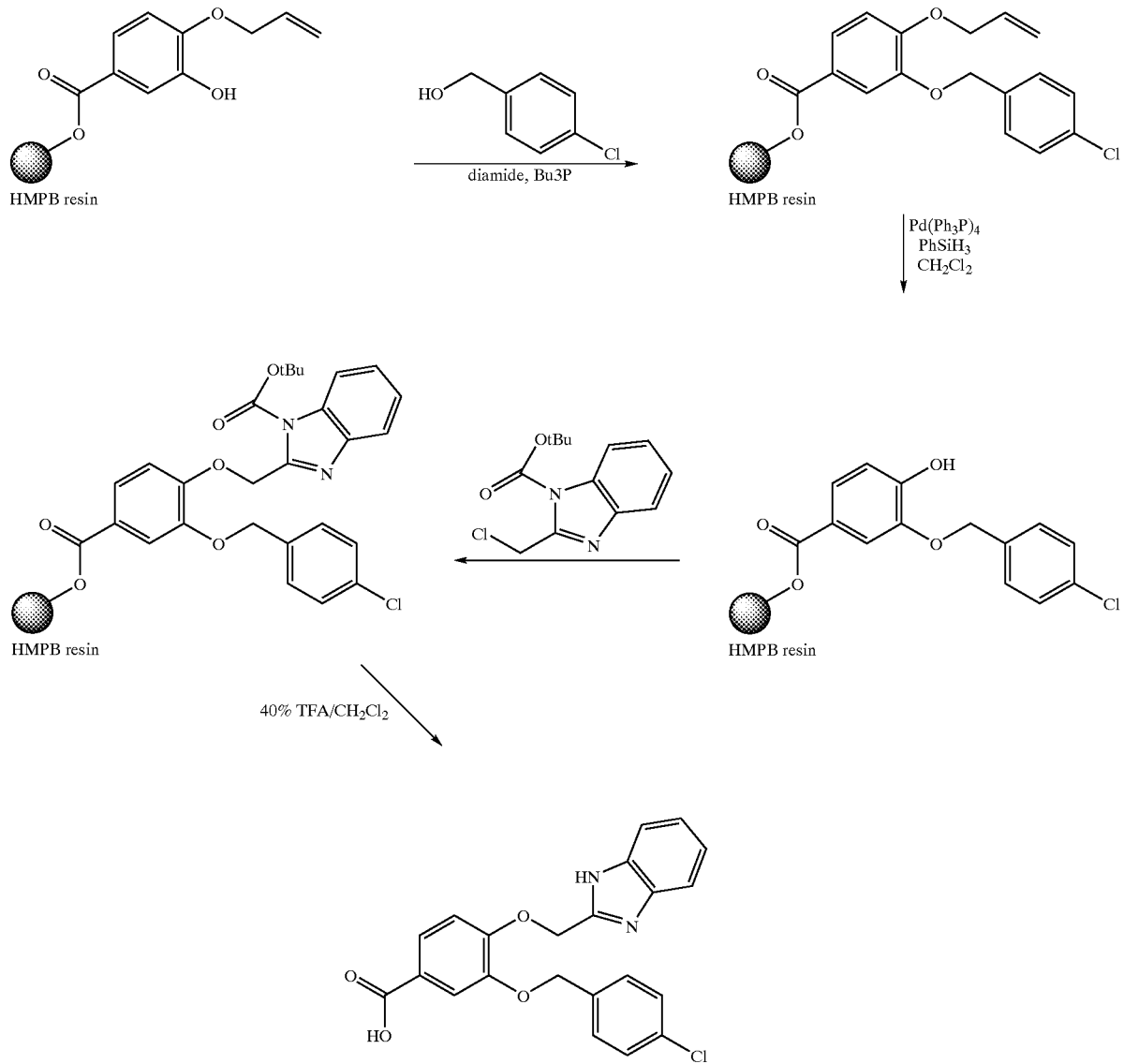

To 0.250 g of HMPB 4-O-allyl-3,4-dihydroxybenzoate resin (loads 0.51 mmol/g) was added 5 ml of distilled THF, 0.180 g of 4-chlorobenzyl alcohol (5 eq.), 0.315 ml of $Bu_3P$ (5 eq.), and finally 220 mg of diamide (5 eq.). The mixture was rotated for 5 hrs in a reaction tube, then the resin was drained and washed five times with DMF, five times with $CH_2Cl_2$, then dried under high vacuum. The resin was swelled in 1.5 ml of $CH_2Cl_2$, and to it was added 0.300 ml of $PhSiH_3$ (20 eq.) and 15 mg of $Pd(Ph_3P)_4$ (0.1 eq.) The mixture was rotated overnight in a reaction tube, then the resin was drained and washed five times with DMF, five times with $CH_2Cl_2$, then dried under high vacuum. This material was swelled in 2.0 ml of DMF, and to it was added 102 mg of 1-t-Boc-2-chloromethylbenzimidazole (3 eq.) and 0.060 ml of DBU (3 eq.) The mixture was rotated overnight in a reaction tube, then the resin was drained and washed five times with DMF, five times with $CH_2Cl_2$, and then cleaved by treating it with 2 ml of 40% trifluoroacetic acid in methylene chloride for 30 minutes. The cleavage solution was drained and the solvent was removed under a nitrogen stream. The residue was purified by HPLC on a YMC-PACK ODS 100×20 mm column, eluting at 20 ml/min on a gradient, beginning with 90/10 water/$CH_3CN$ (0.1% TFA) and ramping up linearly to straight acetonitrile (01% TFA) over an 11 minute run. The fractions containing the product were combined and reduced in volume under a stream of nitrogen, then lyophilized to yield 12 mg of a white, fluffy solid which was analyzed by LC mass spec (409 M+1).

In this manner the compounds were synthesized and characterized by LCMS as shown in Table 3, below:

TABLE 3

Carboxylic Acids Prepared from HMPB
4-O-allyl-3,4-dihydroxybenzoate Resin

| Cmpd. | Reagent 1 | Reagent 2 | Structure of Product | Mass Spec |
|---|---|---|---|---|
| 52 | | | | 485 |
| 53 | | | | 457 |
| 54 | | | | 467 |
| 55 | | | | 443 |

TABLE 3-continued

Carboxylic Acids Prepared from HMPB
4-O-allyl-3,4-dihydroxybenzoate Resin

| Cmpd. | Reagent 1 | Reagent 2 | Structure of Product | Mass Spec |
|---|---|---|---|---|
| 56 | | | | 450 |
| 57 | | | | 427 |
| 58 | | | | 487 |
| 59 | | | | 471 |

TABLE 3-continued

Carboxylic Acids Prepared from HMPB
4-O-allyl-3,4-dihydroxybenzoate Resin

| Cmpd. | Reagent 1 | Reagent 2 | Structure of Product | Mass Spec |
|---|---|---|---|---|
| 60 | (2-fluoro-4-bromobenzyl alcohol) | (tert-butyl 2-(chloromethyl)-1H-benzimidazole-1-carboxylate) | | 471 |
| 61 | (4-chlorobenzyl alcohol) | (tert-butyl 2-(chloromethyl)-1H-benzimidazole-1-carboxylate) | | 450 |
| 62 | (2-nitrobenzyl alcohol) | (tert-butyl 2-(chloromethyl)-1H-benzimidazole-1-carboxylate) | | 374 |
| 63 | (2,4-dichlorobenzyl alcohol) | (tert-butyl 2-(chloromethyl)-6-methoxy-1H-benzimidazole-1-carboxylate) | | 473 |
| 64 | (4-bromo-2-fluorobenzyl bromide) | (tert-butyl 6-chloro-2-(chloromethyl)-1H-benzimidazole-1-carboxylate) | | 505 |

TABLE 3-continued
Carboxylic Acids Prepared from HMPB
4-O-allyl-3,4-dihydroxybenzoate Resin
| Cmpd. | Reagent 1 | Reagent 2 | Structure of Product | Mass Spec |
|---|---|---|---|---|
| 65 | 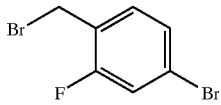 | 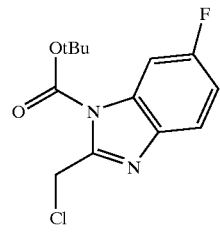 | 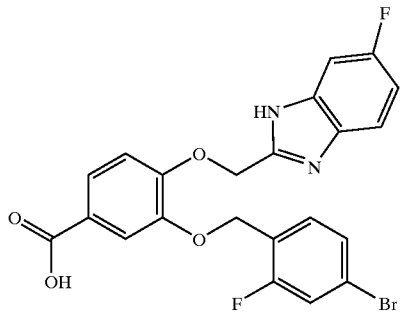 | 489 |
| 66 | 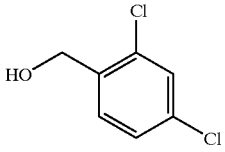 | 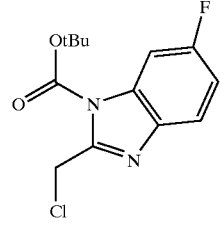 | 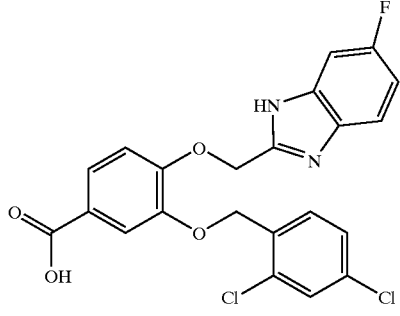 | 461 |
| 67 | 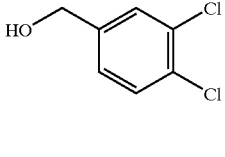 | 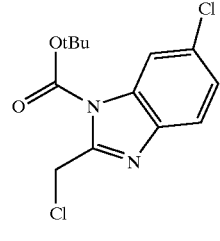 | 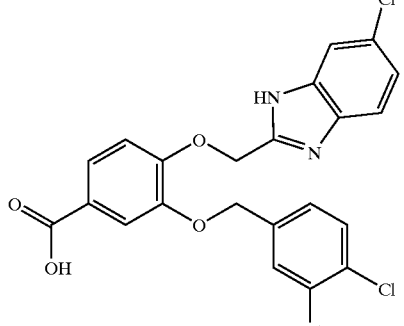 | 477 |
| 68 | 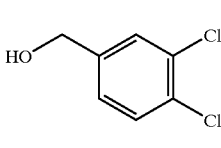 | 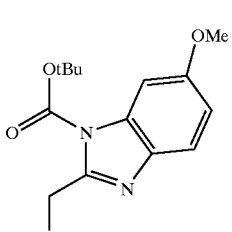 | 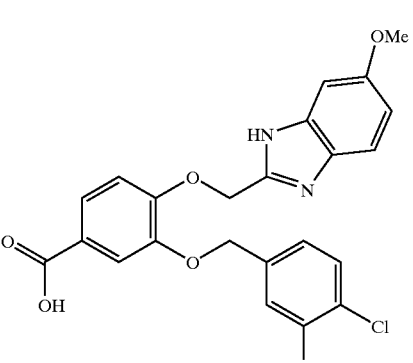 | 473 |

TABLE 3-continued
Carboxylic Acids Prepared from HMPB
4-O-allyl-3,4-dihydroxybenzoate Resin
| Cmpd. | Reagent 1 | Reagent 2 | Structure of Product | Mass Spec |
|---|---|---|---|---|
| 69 | 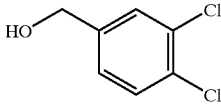 | 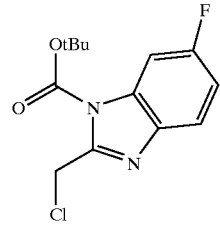 | 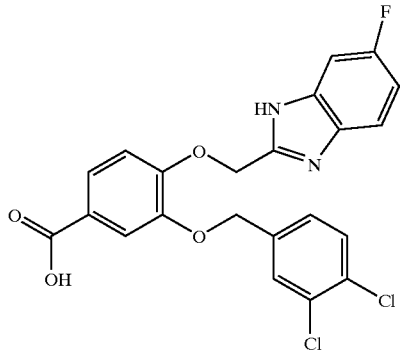 | 461 |
| 70 | 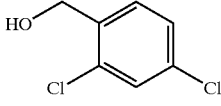 | 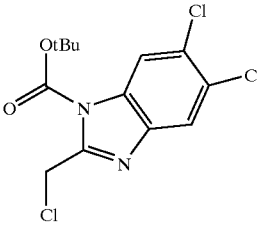 | 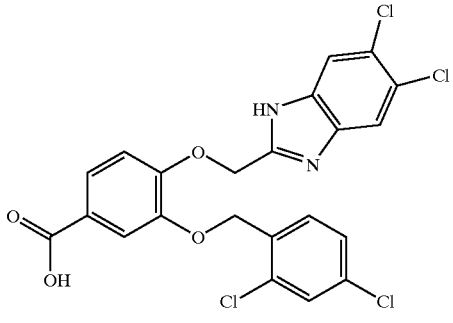 | 511 |
| 71 | 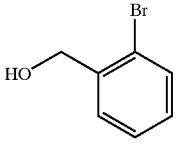 | 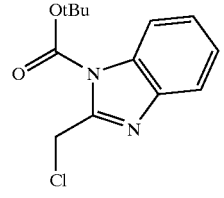 | 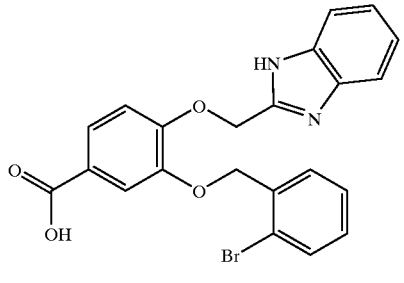 | 453 |
| 72 | 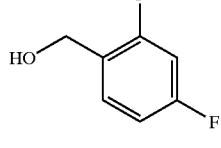 | 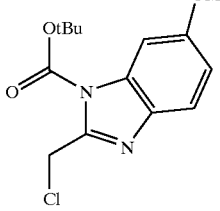 | 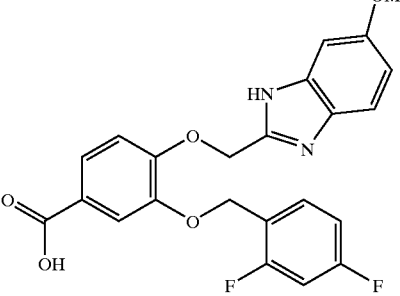 | 411 |

TABLE 3-continued

Carboxylic Acids Prepared from HMPB
4-O-allyl-3,4-dihydroxybenzoate Resin

| Cmpd. | Reagent 1 | Reagent 2 | Structure of Product | Mass Spec |
|---|---|---|---|---|
| 73 | 2-(trifluoromethyl)benzyl alcohol | tert-butyl 2-(chloromethyl)-1H-benzimidazole-1-carboxylate | product structure | 443 |
| 74 | 2-iodobenzyl alcohol | tert-butyl 2-(chloromethyl)-1H-benzimidazole-1-carboxylate | product structure | 501 |
| 75 | 4-bromobenzyl alcohol | tert-butyl 2-(chloromethyl)-1H-benzimidazole-1-carboxylate | product structure | 453 |
| 76 | 2,3-dichlorobenzyl chloride | tert-butyl 2-(chloromethyl)-5-chloro-1H-benzimidazole-1-carboxylate | product structure | 477 |

TABLE 3-continued

Carboxylic Acids Prepared from HMPB
4-O-allyl-3,4-dihydroxybenzoate Resin

| Cmpd. | Reagent 1 | Reagent 2 | Structure of Product | Mass Spec |
|---|---|---|---|---|
| 77 | | | | 477 |
| 78 | | | | 477 |
| 79 | | | | 477 |
| 80 | | | | 487 |

TABLE 3-continued
Carboxylic Acids Prepared from HMPB
4-O-allyl-3,4-dihydroxybenzoate Resin
| Cmpd. | Reagent 1 | Reagent 2 | Structure of Product | Mass Spec |
|---|---|---|---|---|
| 81 | 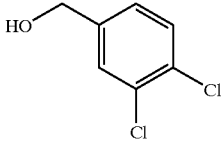 | 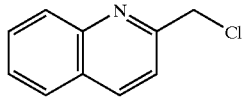 | 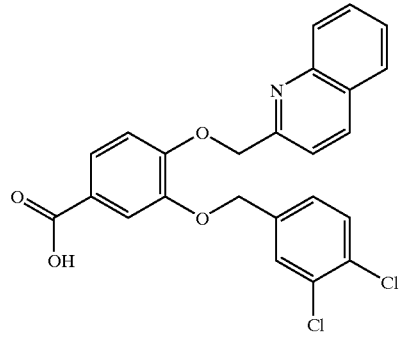 | 453 |
| 82 | 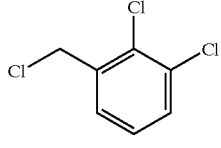 | 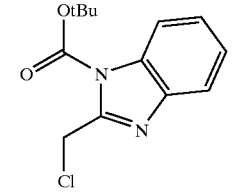 | 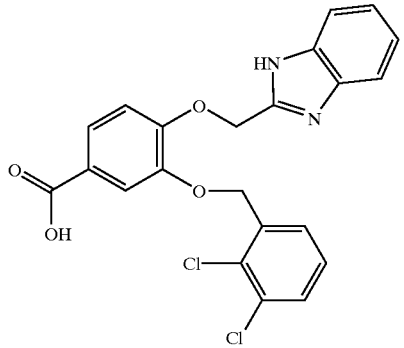 | 443 |
| 83 | 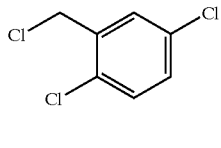 | 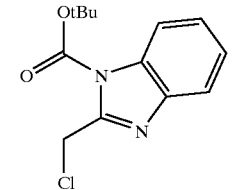 | 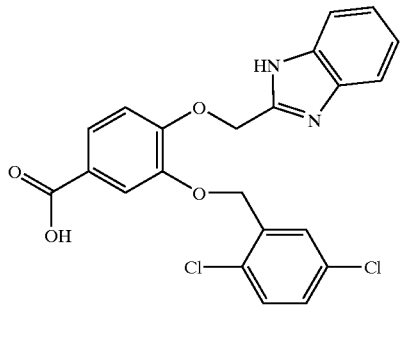 | 443 |
| 84 | 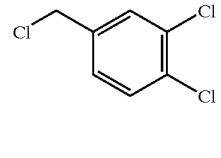 | 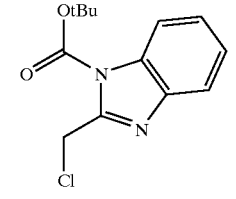 | 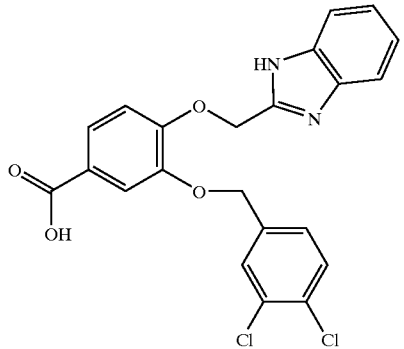 | 443 |

TABLE 3-continued
Carboxylic Acids Prepared from HMPB
4-O-allyl-3,4-dihydroxybenzoate Resin
| Cmpd. | Reagent 1 | Reagent 2 | Structure of Product | Mass Spec |
|---|---|---|---|---|
| 85 | 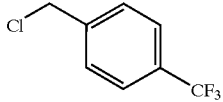 | 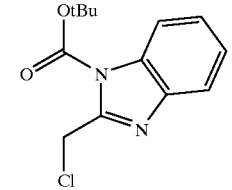 | 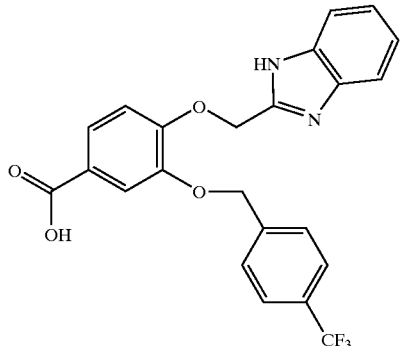 | 443 |
| 86 | 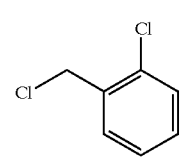 | 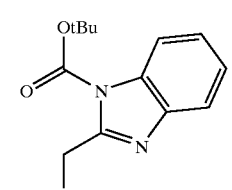 | 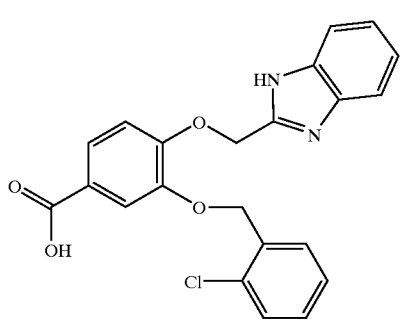 | 409 |
| 87 | 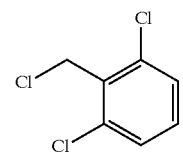 | 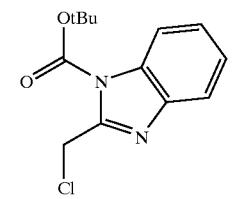 | 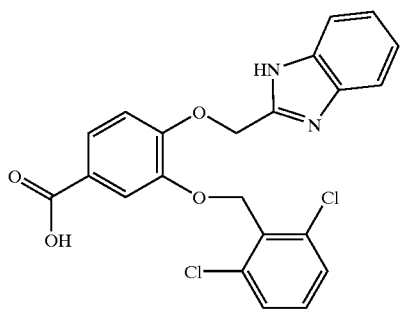 | 443 |
| 88 | 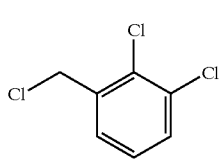 | 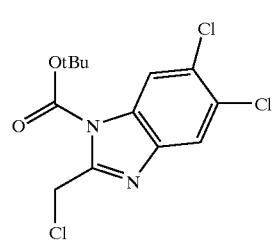 | 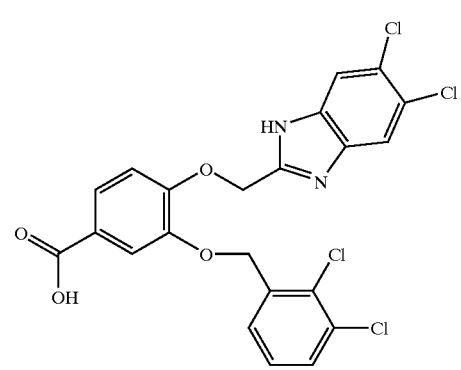 | 511 |

TABLE 3-continued

Carboxylic Acids Prepared from HMPB
4-O-allyl-3,4-dihydroxybenzoate Resin

| Cmpd. | Reagent 1 | Reagent 2 | Structure of Product | Mass Spec |
|---|---|---|---|---|
| 89 | 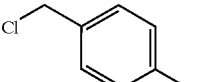 | 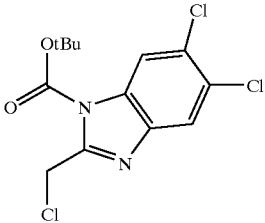 | 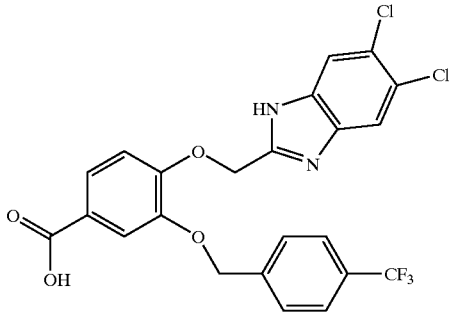 | 511 |

The following two compounds required a slight departure from the standard protocol: Cleavage from the resin was accomplished with 5% TFA in CH2Cl2 for 5 minutes, and gave tBoc protected product. The tBoc was subsequently removed using 2 ml of 1:1 CH2Cl2/2N NH3 in MeOH for 30 minutes. The solvent was removed and the compounds were purified by HPLC in the usual manner. This was necessary because the normal cleavage conditions of 40% TFA/CH2Cl2 for 40 minutes cleaved the p-alkyl benzyl groups

| | | | | |
|---|---|---|---|---|
| 90 | 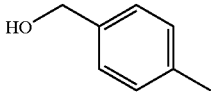 | 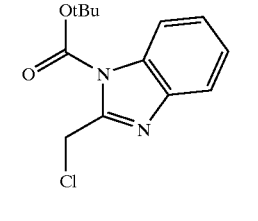 | 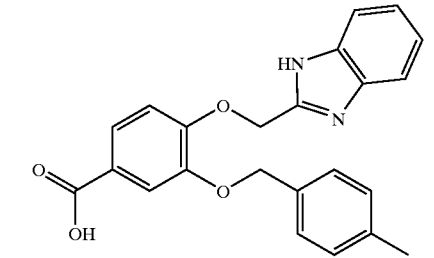 | 389 |
| 91 | 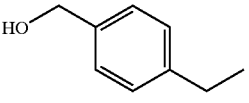 | 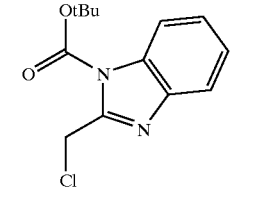 | 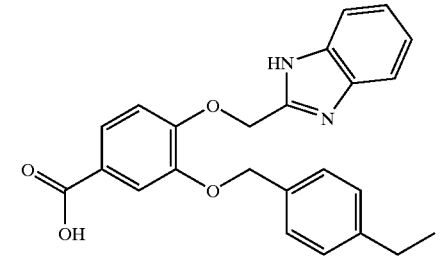 | 421 |

BIOLOGICAL EVALUATION

Enzymatic Activity $IC_{50}$ determinations for the aminoacyl-tRNA synthetases (aaRS) isolated from pathogen or HeLa cells were carried out using a modification of the aaRS charging and trichloroacetic acid precipitation assay described previously (see examples: D. Kern et. al., Biochemie, 61, 1257–1272 (1979) and J. Gilbart et. al. Antimicrobial Agents and Chemotherapy, 37(1), 32–38 (1993)). The aaRS enzymes were prepared via standard cloning and expression methods and partially purified or partially purified from pathogen and HeLa cell extracts. The activity of each aaRS enzyme was standardized as trichloroacetic acid precipitable counts (cpm) obtained at 10 minutes reaction time at $K_m$ concentrations of substrates. For practical purposes, the minimal acceptable value is approximately 2000 cpm per 10 minute reaction.

Preincubations for $IC_{50}$ determinations were initiated by incubating partially purified aaRS extracts in 50 mM HEPES (pH 7.5), 0.1 mM EDTA, 0.05 mg/ml bovine serum albumin, 10 mM dithiothreitol and 2.5% dimethyl sulfoxide with and without test compound (e.g. compound of the invention (preferably a compound of Formula I)) in a final volume of 20 microliters in a microtiter plate for 20 minutes at 25 C. Test compounds were typically present as serial dilutions in concentration ranges of 0.35 nM to 35 $\mu$M. Test compound solutions were prepared by dissolving test compound in 100% dimethyl sulfoxide and diluting to the final concentration with 50 mM HEPES, pH 7.5. $IC_{50}$ determinations were typically performed in duplicate with each experiment containing 4–8 concentrations of inhibitor along with two no inhibitor controls.

$IC_{50}$ incubations were initiated by supplementing the preincubation mixture to a final assay concentration of 10 mM $MgCl_2$, 30 mM KCl, 10 mM KF, 50 mM HEPES (pH 7.5), 20 μM-500 mM ATP, 2–20 μM [$^3$H] amino acid, and 90–180 μM crude tRNA in a final volume of 35 microliters. The reaction was incubated at 25° C. for 5–20 minutes. At specified time points a 15 microliter aliquot was removed and added to a well of a Millipore filtration plate (Multiscreen-FB, MAFB NOB 10) containing 100 microliters of cold 5% (wt/vol) trichloroacetic acid. Trichloroacetic acid precipitable material was collected by filtration on Millipore Multiscreen filtration station, washed twice with cold 5% trichloroacetic acid, twice with water, and dried. Plates were typically allowed to air dry for several hours or they were baked at 50° C. in a vacuum oven for 30 minutes. The radioactivity on the dried plates was quantitated by the addition of Packard Microscint-20 to the wells and counting with a Packard TopCount scintillation counter.

Inhibitor activity was typically reported as a percentage of the control aaRS activity. The $IC_{50}$ value was determined by plotting percent activity versus compound concentration in the assay and identifying the concentration at which 50% of the activity was remaining.

The $IC_{50}$ values (in μM) of some representative compounds of the present invention are listed in Table 4.

Whole Cell Antimicrobial Screens

Compounds were tested for antimicrobial activity against a panel of organisms according to standard procedures described by the National Committee for Clinical Laboratory Standards (NCCLS document M7-A3, Vol. 13, No. 25, 1993/NCCLS document M27-P, Vol. 12, No. 25, 1992). Compounds were dissolved in 100% DMSO and were diluted to the final reaction concentration (0.1 μg/ml–500 μg/ml) in microbial growth media. In all cases the final concentration of DMSO incubated with cells is less than or equal to 1%. For minimum inhibitory concentration (MIC) calculations, 2-fold dilutions of compounds were added to wells of a microtiter plate containing $1\times10^5$ bacteria or fungal cells in a final volume of 200 lambda of an appropriate media (Mueller-Hinton Broth; Haemophilus Test Media; Mueller-Hinton Broth+5% Sheep Blood; or RPMI 1690). Plates were incubated overnight at an appropriate temperature (30° C.–37° C.) and optical densities (measure of cell growth) were measured using a commercial plate reader. The MIC value is defined as the lowest compound concentration inhibiting growth of the test organism.

The MIC values (in μg/ml) of representative compounds of the present invention are listed in Table 4.

TABLE 4

Biological Activity

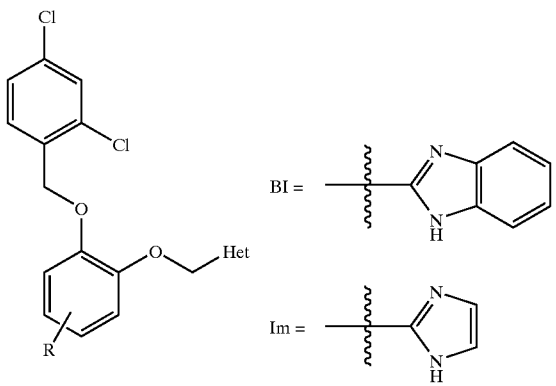

| CB # | $R_1$ | $R_2$ | $R_3$ | $R_4$ | Ar | Het |
|---|---|---|---|---|---|---|
| 126,419 | H | H | H | H | 2,4-$Cl_2C_6H_3$ | BI |
| 126,825 | CHO | H | H | H | 2,4-$Cl_2C_6H_3$ | BI |
| 126,845 | H | H | H | $CH_2OH$ | 2,4-$Cl_2C_6H_3$ | BI |
| 126,898 | H | H | $CO_2H$ | H | 2,4-$Cl_2C_6H_3$ | BI |
| 130,910 | H | H | H | H | 2,4-$Cl_2C_6H_3$ | Im |
| 130,912 | H | $CO_2CH_3$ | H | H | 2,4-$Cl_2C_6H_3$ | BI |
| 130,913 | H | $CO_2H$ | H | H | 2,4-$Cl_2C_6H_3$ | BI |
| 130,920 | H | H | $CONHCH_2CO_2H$ | H | 2,4-$Cl_2C_6H_3$ | BI |
| 130,927 | H | H | (S)—CONHCH($CH_2CO_2H$)$CO_2H$ | H | 2,4-$Cl_2C_6H_3$ | BI |
| 130,966 | H | H | $CONHSO_2CH_3$ | H | 2,4-$Cl_2C_6H_3$ | BI |
| 130,968 | H | H | (S)—CONHCH($CH_2OH$)$CO_2H$ | H | 2,4-$Cl_2C_6H_3$ | BI |
| 130,969 | H | $CONHCH_2CO_2H$ | H | H | 2,4-$Cl_2C_6H_3$ | BI |
| 130,970 | H | (S)—CONHCH($CH_2OH$)$CO_2H$ | H | H | 2,4-$Cl_2C_6H_3$ | BI |
| 130,971 | H | 4-$CONHSO_2CH_3$ | H | H | 2,4-$Cl_2C_6H_3$ | BI |
| 130,972 | H | H | Tetrazole | H | 2,4-$Cl_2C_6H_3$ | BI |
| 130,976 | H | $CH_2CO_2H$ | H | H | 2,4-$Cl_2C_6H_3$ | BI |

TABLE 4-continued

Biological Activity

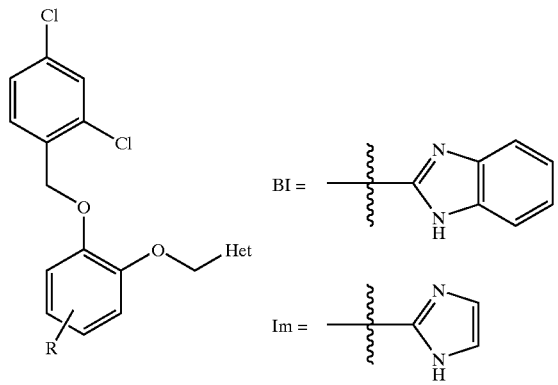

|  | MS | | +/- | IC50 (nM)* | | MIC (μg/mL) | | |
|---|---|---|---|---|---|---|---|---|
| CB # | Calcd | Obsv | ion | Sa | Ef | Sa | Efs | Efm |
| 126,419 | 399.0667 | 399.0649 | + | <500 | <500 | >100 | >100 | >100 |
| 126,825 | 427.0616 | 427.0618 | + | <1000 | <10000 | >100 | >100 | >100 |
| 126,845 | | | + | <10000 | | >100 | >100 | >100 |
| 126,898 | 443.0565 | 443.0577 | + | <500 | <500 | <100 | <10 | <10 |
| 130,910 | 393.0409 | 393.0394 | + | >10000 | >10000 | >100 | >100 | >100 |
| 130,912 | 471.0878 | 471.0900 | + | <500 | <500 | >100 | >100 | >100 |
| 130,913 | 443.0565 | 443.0581 | + | <500 | <500 | <10 | <10 | <10 |
| 130,920 | 498.0624 | 498.0603 | – | <500 | <500 | 100 | <10 | <10 |
| 130,927 | 556.0679 | 556.0686 | – | <500 | <500 | <100 | <100 | <100 |
| 130,966 | 520.0678 | 520.0689 | + | <500 | <500 | 100 | 100 | >100 |
| 130,968 | 528.0729 | 528.0746 | – | <500 | <500 | >100 | >100 | >100 |
| 130,969 | 500.0780 | 500.0770 | + | <500 | <500 | <100 | <10 | <10 |
| 130,970 | 530.0885 | 530.0911 | + | <500 | <500 | 100 | <100 | 100 |
| 130,971 | 520.0678 | 520.0661 | + | <500 | <500 | <100 | 100 | 100 |
| 130,972 | 467.0790 | 467.0772 | + | <500 | <500 | >100 | >100 | >100 |
| 130,976 | 457.0722 | 457.0718 | + | <500 | <500 | <10 | <10 | <10 |

*<500 = 500 nM or less; <1000 = 501–1000 nM; <10000 = 1001–10000 nM; <60000 = 10001–60000 nM

In Vivo Efficacy

Mouse Protection Test

The mouse protection test is an industry standard for measuring the efficacy of a test compound in vivo [for examples of this model see J. J. Clement, et al., *Antimicrobial Agents and Chemotherapy*, 38 (5), 1071–1078, (1994)]. As exemplified below, this test is used to show the in vivo efficacy of the compounds of the present invention against bacteria or fungi.

The in vivo antimicrobial activity of a compound of the invention (preferably a compound of Formula I) hereinafter referred to as test compound, is established by infecting male or female mice (5 mice/dose group×5 doses/compound) weighing 20–25 g intraperitoneally with pathogen inoculum. The inoculum is prepared from a sample of pathogen obtained from the ATCC (for example, ATCC 29213, *S. aureus*; ATCC 14154, *S.aureus*; ATCC 8668, *Strep. pyogenes*; ATCC 25922, *E. coli*; ATCC 29212, *E. faecalis*; ATCC 25238, *M. catarrhalis*; and ATCC 90028, *C. albicans*). Each bacterial strain is grown in its appropriate medium at 37° C. for 18 hr, most strains yielding between $10^8$ and $10^9$ colony forming units (CFU)/ml under these conditions. The overnight culture is serially diluted to an appropriate content and then 0.5 ml of each dilution is added to 4.5 ml of 5% hog gastric mucin to prepare the infecting inoculum. Each mouse is injected with 0.5 ml of the inoculum intraperitoneally (i.p.), five animals per dilution. The 50% lethal dose ($LD_{50}$) and the minimal lethal dose (MLD, the dose causing 100% death of the animals) is calculated on the basis of the number of mice surviving after 7 days. The MLD established for each of the pathogens is used as inoculum dose in the mouse protection tests.

The test compound is dissolved in a sterile vehicle appropriate for its method of delivery (for example, 30% HPB (hydroxypropyl-β-cyclodextrin), pH, 7.4 or 0.05M Tris.HCl). A vehicle group (dose=0) serves as a placebo control for each compound and each pathogen. The dose for the test compound is determined based on the MIC data. A series of dilutions of a test compound is prepared in the vehicle. A group of 5 mice are used for each test compound dose and the vehicle. There are 5–6 doses for each compound. Each animal is used for one experiment only.

Mice are infected i.p. with 0.5 ml of the MLD of pathogen in 5% hog gastric mucin by one researcher and immediately administered compound (s.c., p.o. or i.v. in volumes indicated above) by a second researcher. The 50% protective dose ($PD_{50}$) is calculated from the dose-response curve established on the basis of the numbers of mice surviving for 7 days after treatment. In each experiment, a group of positive control with a commercially available antibiotic for example, is also included.

All of the references, patents and patent publications identified or cited herein are incorporated, in their entirety, by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed:

1. A method of treating a subject afflicted by or susceptible to an infection, wherein said subject is selected from the group consisting of a mammal, a plant and a culture, said method comprising administering to the subject a therapeutically-effective amount of the compound of the Formula:

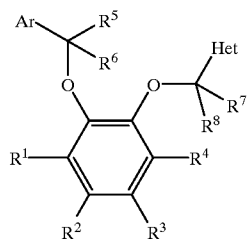

(a) wherein Ar is selected from the group consisting of aryl and heteroaryl;

(b) wherein each of $R^1$, $R^2$, $R^3$, and $R^4$ is independently selected from the group consisting of hydrido, alkyl, cyano, heteroaryl, hydroxy, amino, acylamino, halo, alkoxy, aryloxy, carboxyamido, alkenyl, cycloalkyl, heterocyclyl, acyl, acyloxy, carboalkoxy, carboxy, thio, sulfinyl, sulfonyl and sulfoxy, provided that at least two of $R^1$, $R^2$, $R^3$ and $R^4$ is hydrido;

(c) wherein each of $R^5$, $R^6$, $R^7$, and $R^8$ is independently selected from the group consisting of hydrido and lower alkyl;

(d) wherein Het is selected from the group consisting of

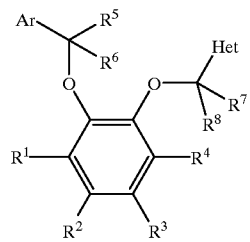

wherein each of $R^{11}$, $R^{12}$ and $R^{13}$ is independently selected from the group consisting of nitro, halo, hydroxy, lower amino, lower alkyl, lower alkoxy, aryloxy, lower carboalkoxy, sulfinyl, sulfonyl, carboxy, lower thio, and sulfoxy.

2. The method of claim 1 wherein Ar is aryl and pharmaceutically-acceptable salts thereof.

3. The method of claim 1 wherein each of $R^1$, $R^2$, $R^3$, and $R^4$ is independently selected from the group consisting of hydrido, carboxyl, alkyl, carboxyamido, N-acylaminosulfonyl, N-sulfonylcarboxyamido, and alkoxy; and pharmaceutically-acceptable salts thereof.

4. The compound of claim 3 wherein each of $R^1$, $R^2$, $R^3$, and $R^4$ is independently selected from the group consisting of —$(CH_2)_mCO_2H$—, —$(CH_2)_mCONHCH(R^9)CO_2H$—, —$CONHSO_2R^{10}$—, and —$O(CH_2)_mCO_2H$; wherein each of $R^9$ and $R^{10}$ is independently selected from the group consisting of alkyl and halo substituted alkyl; wherein m is selected from the group consisting of 0, 1 and 2; and pharmaceutically-acceptable salts thereof.

5. The method of claim 1 wherein the infection is a bacterial infection.

6. The method of claim 1 wherein the infection is a fungal infection.

7. The method of claim 1 wherein the subject is a mammal.

8. The method of claim 1 wherein the mammal is a human.

* * * * *

UNITED STATES PATENT AND TRADEMARK OFFICE
CERTIFICATE OF CORRECTION

PATENT NO. : 6,545,015 B2
DATED : April 8, 2003
INVENTOR(S) : Milton L. Hammond et al.

It is certified that error appears in the above-identified patent and that said Letters Patent is hereby corrected as shown below:

Column 90,
Lines 2-18, should read:

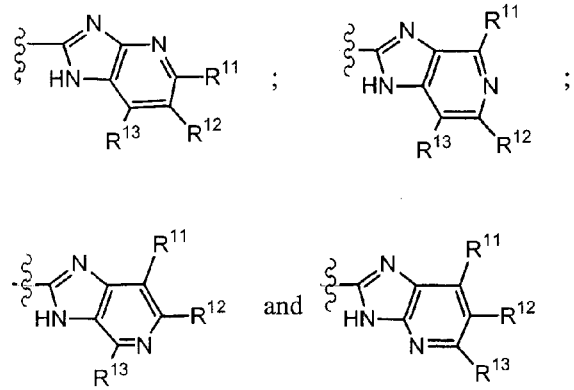

wherein each of $R^{11}$, $R^{12}$ and $R^{13}$ is independently selected from the group consisting of nitro, halo, hydroxy, lower amino, lower alkyl, lower alkoxy, aryloxy, lower carboalkoxy, sulfinyl, sulfonyl, carboxy, lower thio, and sulfoxy.

Signed and Sealed this

Twenty-third Day of March, 2004

JON W. DUDAS
*Acting Director of the United States Patent and Trademark Office*